US012109011B2

(12) United States Patent
Ikuta et al.

(10) Patent No.: US 12,109,011 B2
(45) Date of Patent: Oct. 8, 2024

(54) BIOLOGICAL SIGNAL MEASURING DEVICE

(71) Applicant: SONY GROUP CORPORATION, Tokyo (JP)

(72) Inventors: Tomoya Ikuta, Tokyo (JP); Atsushi Ito, Tokyo (JP); Kazunari Yoshifuji, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 551 days.

(21) Appl. No.: 17/311,024

(22) PCT Filed: Dec. 12, 2019

(86) PCT No.: PCT/JP2019/048637
§ 371 (c)(1),
(2) Date: Jun. 4, 2021

(87) PCT Pub. No.: WO2020/122164
PCT Pub. Date: Jun. 18, 2020

(65) Prior Publication Data
US 2022/0015649 A1    Jan. 20, 2022

(30) Foreign Application Priority Data
Dec. 14, 2018    (JP) .................................. 2018-234519

(51) Int. Cl.
*A61B 5/0295*   (2006.01)
*A61B 5/00*     (2006.01)
*A61B 5/026*    (2006.01)

(52) U.S. Cl.
CPC .......... *A61B 5/0295* (2013.01); *A61B 5/0261* (2013.01); *A61B 5/681* (2013.01); *A61B 2562/0238* (2013.01)

(58) Field of Classification Search
CPC ........ A61B 2562/0238; A61B 5/02427; A61B 5/02438; A61B 5/0261; A61B 5/0295; A61B 5/681; A61B 5/6824
See application file for complete search history.

(56) References Cited

U.S. PATENT DOCUMENTS

2008/0275322 A1    11/2008   Kim et al.
2017/0188953 A1    7/2017    Jeon et al.
(Continued)

FOREIGN PATENT DOCUMENTS

DE    102016218060 A1    7/2017
EP        2837327 A1     2/2015
(Continued)

OTHER PUBLICATIONS

Partial Supplementary European Search Report of EP Application No. 19894562.8, issued on Apr. 26, 2022, 18 pages.
(Continued)

*Primary Examiner* — Michael T Rozanski
(74) *Attorney, Agent, or Firm* — CHIP LAW GROUP

(57) ABSTRACT

A biological signal measuring device that includes a light emitting unit that includes at least a first light emitting element and a second light emitting element that irradiate a biological surface, and a light receiving unit that includes at least one light receiving element that receives light scattered in a living body by light emitted from the light emitting unit, and outputs biological information that is a light intensity signal measured by the light receiving element. The biological signal measuring device is capable of performing both pulse measurement and blood flow measurement with high accuracy.

18 Claims, 13 Drawing Sheets

(56) References Cited

U.S. PATENT DOCUMENTS

| | | |
|---|---|---|
| 2017/0251936 A1 | 9/2017 | Sawado et al. |
| 2017/0273570 A1 | 9/2017 | Kojima et al. |
| 2017/0273636 A1 | 9/2017 | Umekawa et al. |
| 2018/0070830 A1 | 3/2018 | Sutin et al. |

FOREIGN PATENT DOCUMENTS

| | | |
|---|---|---|
| JP | 7-265284 A | 10/1995 |
| JP | 2008-264327 A | 11/2008 |
| JP | 2012-176225 A | 9/2012 |
| JP | 2017-176264 A | 10/2017 |
| JP | 2018-068428 A | 5/2018 |
| KR | 10-0848118 B1 | 7/2008 |
| KR | 10-1736997 B1 | 5/2017 |
| WO | 2013/153664 A1 | 10/2013 |
| WO | 2017/098872 A1 | 6/2017 |

OTHER PUBLICATIONS

Abdollahi, et al., "Evaluation of optical interference in a combined measurement system used for assessment of tissue blood flow", Progress in Biomedical Optics and Imaging—Proceedings of SPIE, XP060048823, vol. 9315, Mar. 5, 2015, 6 pages.

International Search Report and Written Opinion of PCT Application No. PCT/JP2019/048637, issued on Feb. 18, 2020, 13 pages of ISRWO.

BIOLOGICAL SIGNAL MEASURING DEVICE

CROSS REFERENCE TO RELATED APPLICATIONS

This application is a U.S. National Phase of International Patent Application No. PCT/JP2019/048637 filed on Dec. 12, 2019, which claims priority benefit of Japanese Patent Application No. JP 2018-234519 filed in the Japan Patent Office on Dec. 14, 2018. Each of the above-referenced applications is hereby incorporated herein by reference in its entirety.

TECHNICAL FIELD

The present technology relates to a biological signal measuring device.

BACKGROUND ART

In the medical field and the like, there are many measuring devices that acquire biological information from the human body, and the biological information includes pulses, pulse waves, blood flows, and blood pressures, for example.

For example, a device that measures pulses is a photoplethysmographic device (photoplethysmography: PPG) or the like. This photoplethysmographic device measures changes in the volume of the blood vessels, taking advantage of the light absorptive property of hemoglobin in blood. For example, Patent Document 1 suggests a pulse measuring element that includes a special light guiding member capable of increasing measurement accuracy and the like. Further, Patent Document 2 suggests a biological information detecting device that includes a special prism capable of reducing the burden on the user's operability and the like, and detects information about a volume pulse wave from a biological portion.

For example, a device that measures a blood flow may be a laser Doppler blood flowmeter (Laser Doppler Flowmetry: LDF) or the like. For example, Patent Document 3 suggests an information processing device that includes an estimation unit that estimates blood flow information on the basis of relationship information indicating the relationship between two different types of blood flow information.

Further, Patent Document 4 suggests a biological information measuring device that includes: one LD light source that switches between laser oscillation light and natural light, and performs light emission; one light receiving element that receives each scattered light and outputs a photocurrent; and a drive measuring circuit that measures the blood flow in a living body when the light source emits laser oscillation light, and measures the pulses in the living body when the light sources emits natural light.

CITATION LIST

Patent Documents

Patent Document 1: WO 2017/098872 A
Patent Document 2: Japanese Patent Application Laid-Open No. 2012-176225
Patent Document 3: Japanese Patent Application Laid-Open No. 2018-68428
Patent Document 4: Japanese Patent Application Laid-Open No. 2008-264327

SUMMARY OF THE INVENTION

Problems to be Solved by the Invention

The present technology primarily aims to provide a small-sized biological signal measuring device capable of performing both pulse measurement and blood flow measurement with high accuracy.

Solutions to Problems

The present technology can provide a biological signal measuring device that includes:

a light emitting unit that includes at least a first light emitting element and a second light emitting element that irradiate a biological surface; and a light receiving unit that includes at least one light receiving element that receives light scattered in a living body by light emitted from the light emitting unit, and outputs biological information that is a light intensity signal measured by the light receiving element. The biological signal measuring device may perform blood flow measurement and pulse measurement.

The first light emitting element may include at least a light source that emits light having a long coherence length, and the second light emitting element may include at least a light source that emits light having a short coherence length.

The light receiving unit may include at least one light receiving element that measures both an instantaneous value and an interval value, or two light receiving elements that measure an instantaneous value and an interval value, respectively.

The light emitting elements may be designed to be driven, with the light emitting time being split.

The light receiving elements may be designed to be driven, with the light receiving time being split.

The light receiving unit may include one light receiving element that measures both an instantaneous value and an interval value, and the light receiving unit may include a light reception adjustment mechanism for the light receiving element to cope with biologically scattered light generated by each light emission from the light emitting unit.

The light reception adjustment mechanism of the light receiving unit may be designed to reduce the light receiving area of light having a long coherence length.

The light reception adjustment mechanism of the light receiving unit may use at least one of an optical filter, a multi-segment photodiode, or a liquid crystal shutter.

Further, the distances between the light emitting elements and the light receiving element that receives the biologically scattered light generated by light emission may be adjusted.

Further, the distance between the biological surface and the light receiving surface of the light receiving element may be adjusted.

The first light emitting element may be designed to emit continuous light between light emissions from the second light emitting element.

The second light emitting element may be designed to emit pulsed light.

The light receiving unit may include at least two light receiving elements that are a first light receiving element for interval value measurement and a second light receiving element for instantaneous value measurement, and the light receiving unit may be designed to receive biologically scattered light generated by each light emission from the light emitting unit with the first light receiving element and measure an interval value, and be designed to receive light with the second light receiving element and measure an instantaneous value.

The first light receiving element for interval value measurement may be designed to receive biologically scattered light generated by light having a long coherence length of the light emitting elements, the second light receiving element for instantaneous value measurement may be designed to receive biologically scattered light generated by light having a long coherence length of the light emitting elements and biologically scattered light generated by light having a short coherence length of the light emitting elements, and the light receiving area of the first light receiving element may be smaller than the light receiving area of the second light receiving element.

The first light emitting element may be designed to emit continuous light between light emissions from the second light emitting element, the second light emitting element may be designed to emit pulsed light, the first light receiving element may be designed to receive biologically scattered light generated by the continuous light emission from the first light emitting element, and measure an interval value, and the second light receiving element may be designed to receive biologically scattered light generated by the pulsed light emission from the second light emitting element and part of the biologically scattered light generated by the continuous light emission from the first light emitting element, and measure an instantaneous value.

The first light emitting element may be designed to randomly emit continuous light and pulsed light between light emissions from the second light emitting element, the second light emitting element may be designed to emit pulsed light, the first light receiving element may be designed to receive biologically scattered light generated by the continuous light emission from the first light emitting element, and measure an interval value, and the second light receiving element may be designed to receive biologically scattered light generated by the pulsed light emission from the second light emitting element and biologically scattered light generated by the pulsed light emission from the first light emitting element, and measure an instantaneous value.

Further, the distances between the light emitting elements and the light receiving element that receives the biologically scattered light generated by light emission may be adjusted.

Further, the distance between the biological surface and the light receiving surface of the light receiving element may be adjusted.

MODES FOR CARRYING OUT THE INVENTION

Figure 1:
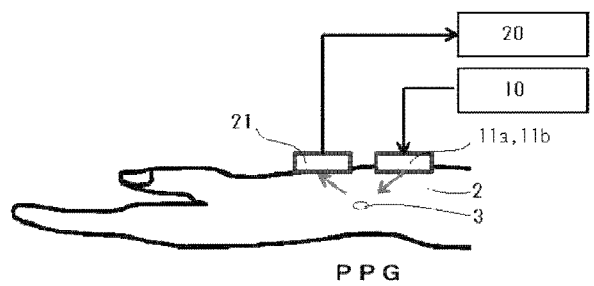
FIG. 1 is a schematic diagram showing an example of a reflective photoplethysmographic (PPG) measuring system in the present technology.

The following is a description of preferred embodiments for carrying out the present technology, with reference to the accompanying drawings.

The embodiments described below are typical examples of embodiments of the present technology, and do not narrow the interpretation of the scope of the present technology. Note that explanation will be made in the following order. Note that, in the drawings, the same or equivalent components or members are denoted by the same reference numerals, and repetitive explanation of them will be skipped as appropriate.

1. Biological signal measuring device according to the present technology
   1-1. Outline of the biological signal measuring device according to the present technology
   1-2. Biological signal measuring device 1 according to the present technology
      1-2(1). Biological surface 2
      1-2(2). Light emitting unit 10
      1-2(3). Light receiving unit 20
      1-2(4). Signal processing unit 50
   1-3. Biological signal measuring device 1 according to a first embodiment
      1-3(1). Light reception adjustment mechanism
      1-3(2). Example 1 of a biological signal measuring device according to the first embodiment
      1-3(3). Example 2 of a biological signal measuring device according to the first embodiment
      1-3(4). Example 3 of a biological signal measuring device according to the first embodiment
      1-3(5). Example 4 of a biological signal measuring device according to the first embodiment
      1-3 (6). Example 5 of a biological signal measuring device according to the first embodiment
      1-3 (7). Example 6 of a biological signal measuring device according to the first embodiment
      1-3 (8). Examples 7 and 8 of biological signal measuring devices according to the first embodiment
   1-4. Biological signal measuring device 1 according to a second embodiment
      1-4 (1). Example 1 of a biological signal measuring device according to the second embodiment
      1-4 (2). Example 2 of a biological signal measuring device according to the second embodiment
      1-4 (3). Example 3 of a biological signal measuring device according to the second embodiment
      1-4 (4). Example 4 of a biological signal measuring device according to the second embodiment
2. Diological information processing apparatus

1. Biological Signal Measuring Device According to the Present Technology

Since pulses and blood flows reflect changes in the cardiovascular system of the human body they are a set of very useful biological information in observing the state of the human body.

A conventional reflective PPG device includes an LED as a light emitting element (a light source) and a PD as a light receiving element (a photoreceiver), and is designed to emit LED light toward a living body, and measure, with the PD, the scattered light (non-coherent light) reflected in the living body. Since hemoglobin exists in the blood in the living body and characteristically absorbs incident light, changes caused in the volume of the blood vessels by the pulsation of the heart are sensed in chronological order, and thus, pulse signals can be measured.

Meanwhile, a conventional LDF device includes an LD as a light emitting element (a light source) and a PD as a light receiving element (a photoreceiver), and is designed to emit LD light toward a living body, and measure, with the PD, interference by light that has no Doppler shifts and is reflected by stationary tissue in the living body, and light that has a Doppler shift (coherent light) and is reflected from moving blood. The interfering light is measured as a beat signal, and the beat signal is divided into time windows and is subjected to Fourier transform, so that the frequency spectrum of each time is obtained. In the case of a living body, the frequency spectrum of the beat signal is distributed from about several tens of Hz to several tens of kHz, and its shape changes with the blood flow rate. Further, the value obtained by performing normalization with the intensity of received light on the value obtained by multiplying the frequency spectrum in a certain time window by frequency, followed by integration, is proportional to the blood flow rate. Thus, the change corresponding to the blood flow rate can be measured.

Conventionally, a PPG device for measuring pulses and an LDF device for measuring blood flows have been developed as separate devices. In a case where these two pieces of biological information are to be measured at the same time, these two devices must be installed and used. Therefore, the resultant device becomes larger in size due to the two devices, and occupies a large area when attached to a living body.

For example, according to Patent Document 4 (Japanese Patent Application Laid-Open No. 2008-264327), an LD light source is always required for LDF measurement. Therefore, the output of the LD light source is lowered, so that spontaneous emission light such as LED light is emitted, and the LD light source can also be used for PPG measurement. Specifically, the LD light source is made to emit light at an electric current threshold or lower so that spontaneous emission light is emitted. The LD light source is driven in a time-split manner so as to emit LD light when the device functions as an LDF device, and emit spontaneous emission light when the device functions as a PPG device. Thus, these two devices are integrated. Further, in the biological information measuring device of Patent Document 4, only one LD light source is provided, one light receiving element for LDF measurement is used also for PPG measurement, and one shared light receiving element is provided (particularly, see FIG. 1 of Patent Document 4).

As described above, Patent Document 4 uses only an LD light source as the light source. The problem in this case is that the amount of light is reduced because the electric current is reduced at the time of LED light emission. Therefore, the inventor considered that there was a possibility that the influence of signal noise during PPG measurement would increase. In a case where oxygen saturation is to be measured in PPG, at least two types of wavelengths are required. However, in Patent Document 4, there is only one kind of light source, and there is also one kind of wavelength during light emission. Therefore, the inventor considered that oxygen saturation could not be measured, and further, signals for noise removal could not be measured either.

<1-1. Outline of the Biological Signal Measuring Device According to the Present Technology>

The present inventor discovered that, in a biological signal measuring device, it is important to use at least two light emitting elements, use at least one light receiving element that receives light scattered in a living body, and further output a light intensity signal measured by the light receiving element as biological information. The present technology then provides a biological signal measuring device including: a light emitting unit that includes at least a first light emitting element and a second light emitting element that irradiate a biological surface; and a light receiving unit that includes at least one light receiving element that receives light scattered in a living body by light emitted from the light emitting unit, and outputs biological information that is a light intensity signal measured by the light receiving element.

With the above configuration of the present technology, a light source and a photoreceiver are shared between LDF measurement and PPG measurement, and accordingly, two devices that are a device for LDF measurement and a device for PPG measurement can be integrated into one device. Therefore, the present technology preferably provides a biological signal measuring device for blood flow measurement and pulse measurement. The device of the present technology can be made smaller in size, and the contact area can be reduced when the user wears the device. Thus, the burden on the wearer is reduced. Also, as the device size is reduced, power consumption is also reduced.

In the present technology, two light emitting elements are used, so that multi-measurement can be performed with a small-sized device while being less affected by PPG signal noise. Further, in the present technology, the light source can have two wavelengths for PPG measurement, and thus, measurement of signals for noise removal can also be performed. Also, in PPG measurement according to the present technology, it is possible to measure oxygen saturation by using two appropriate different wavelengths.

The present technology is preferably designed not only to use at least two light emitting elements, but also to: (a) adjust light reception of one light receiving element to control LDF light reception and/or PPG light reception: and/or (b) control driving related to light emission and light reception so that an interval value and/or an instantaneous value can be measured with two light receiving elements. In this case, the light receiving unit used in the present technology preferably includes (a) at least one light receiving element, and/or (b) at least two light receiving elements. Further, the light receiving unit is preferably designed to output a light intensity signal measured by one light receiving element of (a) as biological information. Also, the light receiving unit is preferably designed to output light intensity signals measured by two light receiving elements of (b) as biological information. At least one light emitting element of the present technology is preferably a light source that emits at least light having a long coherence length. Further, at least one light emitting element of the present technology is preferably a light source that emits at least light having a short coherence length. The light receiving unit preferably includes one light receiving element that performs both instantaneous value measurement and interval value measurement, or two light receiving elements that measure an instantaneous value and an interval value, respectively. The light emitting elements are preferably designed to be driven, with the light emitting time being split. The light receiving elements are preferably designed to be driven, with the light receiving time being split.

By the present technology, a light reception adjustment mechanism (more preferably a light receiving area adjustment mechanism) is used so that one light receiving element (PD) can be used for both LDF measurement and PPG measurement. Thus, influence of noise in signals on both LDF and PPG can be reduced. Further, by the present technology, the device can be made smaller in size, and pulse measurement and blood flow measurement can be simultaneously performed in a sophisticated manner. By the present technology, the number of PDs to be driven becomes smaller, and thus, power consumption is lowered. As the PD areas can be made suitable for both LDF and PPG, signals can be acquired with high accuracy (see the first embodiment described later).

By the present technology, driving of components related to light emission (at least two light emitting elements) and components related to light reception (at least two light receiving elements) is controlled, so that sufficient light emission intensity for PPG measurement can be secured, and LDF and PPG measurement can be performed with high accuracy. A light source having a long coherence length is suitable for at least one of the light emitting elements. It is more preferable to include at least two light receiving elements that are a light receiving element that measures an instantaneous value in response to light having a short coherence length of a light emitting element, and a light receiving element that measures an interval value in response to light having a long coherence length of a light emitting element. It is even more preferable to include a light receiving element that measures this instantaneous value in response to light having a long coherence length emitted by the light emitting element having a long coherence length, and thus, measure the instantaneous value. Further, by the present technology, a light source is shared, and accordingly, the device that integrates LDF measurement and PPG measurement is made smaller in size. As the number of light sources to be driven becomes smaller, power consumption is lowered accordingly. By the present technology, the intensity of PPG light emission is sufficient, and thus, signals can be acquired with high accuracy. As two kinds of PPG emission wavelengths can be adopted, it is possible to measure oxygen saturation and signals for noise removal (see the second embodiment described later).

<1-2. Biological Signal Measuring Device 1 According to the Present Technology>

A biological signal measuring device according to the present technology and each component thereof will be described below in greater detail, but the present technology is not limited to this.

Figure 2:
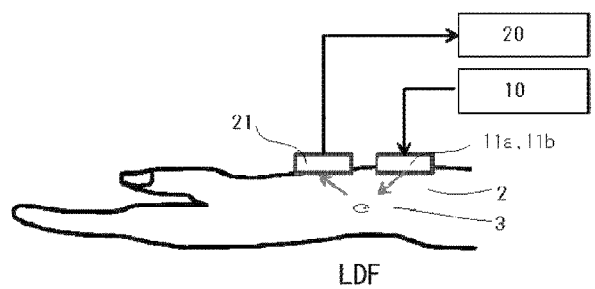
FIG. 2 is a schematic diagram showing an example of a measuring system of a laser Doppler blood flowmeter (LDF) in the present technology.

An example of a biological signal measuring device 1 according to the present technology is now described with reference to FIGS. 1 and 2, but the present technology is not limited to this.

The biological signal measuring device 1 according to the present technology includes: a light emitting unit 10 including at least a first light emitting element 11a and a second light emitting element 11b that irradiate a biological surface 2; and a light receiving unit 20 that includes at least one light receiving element 21 that receives light scattered in a living body by the light emitted from the light emitting unit 10, and outputs biological information that is a light intensity signal measured by the light receiving element 21. With this configuration, it is possible to provide a biological signal measuring device capable of performing both pulse measurement and blood flow measurement with high accuracy. Note that the effects described herein are not necessarily limited thereto, but may also include any of the effects described in the present specification.

Also, with this configuration, it is possible to store two light emitting elements and at least one or two light receiving elements in a housing 40, and further, a light reception adjustment mechanism is also contained in the housing 40 as needed. As these components are integrated with the housing, the device can be made smaller in size. Further, the light emitting unit 10, the light receiving unit 20, a signal processing unit 50, and the like may be contained in the housing 40. Also, some or all of the functions to be executed by the light emitting unit 10, the light receiving unit 20, the signal processing unit 50, and the like may be disposed outside the housing 40, or may be disposed in an accessible information processing device (such as a server or the like, for example).

Further, in the present technology, the biological signal measuring device 1 is preferably a biological signal measuring device for blood flow measurement and pulse measurement. The present technology is more preferably photoplethysmography (PPG) measurement (preferably a reflective type) and/or a laser doppler flowmetry (LDF) measurement. In addition to the above, the present technology is also capable of oxygen saturation measurement and the like.

<1-2(1). Biological Surface 2>

In the present technology, the biological surface 2 for acquiring biological information is the surface of a part (a measurement area) such as a hand, an arm, the neck, or a foot of the person to be measured, for example, but are not limited to this example.

A measurement area of the present technology is preferably a site at which biological information about the subject can be obtained. More specifically, a site at which pulse information and/or blood flow information regarding the pulse and/or blood flow of the subject can be obtained is more preferable, and oxygen saturation information can also be obtained at the site.

<1-2(2). Light Emitting Unit 10>

The light emitting unit 10 according to the present technology includes at least two light emitting elements 11. Further, the light emitting elements 11 are preferably designed to be driven in a time-split manner.

The light emitting elements are preferably light sources having their wavelength of use in a visible light region, a near-infrared region, or an infrared region. The light emitting elements may be laser diode (LD) light sources, light emitting diode (LED) light sources, xenon light sources, or the like, for example, but are not limited to this example. These light sources may be those whose irradiation wavelength can be changed, or those which emit light of a specific wavelength. The LED light sources may be light sources that are capable of emitting light in an ultraviolet wavelength region, a visible light region, an infrared region, or the like, and are capable of emitting monochromatic light like white LEDs, red LEDs, or blue LEDs, or light of these colors. Note that LD light sources are classified as light sources having a long coherence length, and LED light sources are classified as light sources having a short coherence length. Alternatively, the light emitting unit 10 may be designed to adjust light emitted from a light source to a desired irradiation wavelength with an optical filter or the like.

The light emitting unit 10 can use a small laser or the like to emit coherent light, and is capable of emitting light of a specific wavelength (a wavelength around 850 nm, for example) from the light emitting elements 11 that are LDs, for example. The light emitting unit 10 can also emit visible light or the like from the LED light emitting elements 11 to emit light having a short coherence length. Note that light such as sunlight, light from a light bulb, light from a fluorescent lamp, or light from an LED is light that is low in coherence and is close to completely incoherent light, but in general, such light may be expressed as non-coherent light in some cases.

More preferably, the light emitting unit 10 includes at least the first light emitting element 11$a$ and the second light emitting element 11$b$. Further, the first light emitting element 11$a$ and the second light emitting element 11$b$ are preferably designed to be driven, with the light emitting time being split. The first light emitting element 11$a$ and the second light emitting element 11$b$ may also be designed to perform continuous light emission and/or pulsed light emission. Note that, to distinguish between the two light emitting elements, they are referred to as the first and second light emitting elements for convenience, but are not necessarily referred to in this manner. As for the light emitting elements 11 of the present technology, at least one of the light emitting elements is preferably a light source (such as a LD light source, for example) having a long coherence length.

Further, it is preferable to use at least two kinds of light sources having different coherence lengths as the light emitting elements 11 of the present technology. Preferably, one of the light emitting elements is a light source that emits at least light having a long coherence length, and the other one is a light source that emits at least light having a short coherence length. More specifically, in the present technology, the first light emitting element 11$a$ is preferably a light source that emits at least light having a long coherence length, and/or the second light emitting element 11$b$ is preferably a light source that emits at least light having a short coherence length. With this arrangement, LDF measurement and PPG measurement can be performed with higher accuracy.

Further, the light emitting elements 11 of the present technology are preferably at least two kinds of light sources capable of emitting light of different wavelengths from each other, separately or at the same time. With this arrangement, the influence of body movement can be measured, light emission with different wavelengths can be performed to remove noise, and oxygen saturation can also be measured.

The light emitting unit 10 may be designed so that light emission (emission wavelength, timing, and the like) can be controlled by the signal processing unit 50. At this stage, the signal processing unit 50 preferably performs control so that the light emitting elements 11 are synchronized with the light receiving element described later.

In the present technology, at least two light emitting elements 11, or at least three light emitting elements 11, such as LDs or LEDs, may be provided in a biological information processing apparatus (a measurement module or the like, for example). Further, in the present technology, one or more light emitting units 10 each including at least two light emitting elements 11 may be provided in a biological information processing apparatus (a measurement module or the like, for example).

<1-2(3). Light Receiving Unit 20>

The light receiving unit 20 according to the present technology includes at least one light receiving element 21. Further, the light receiving element 21 is preferably designed to be driven in a time-split manner. The light receiving unit 20 preferably includes at least one or at least two light receiving elements 21. The light receiving unit 20 is designed to perform measurement with the light receiving elements 21 that receive the light scattered in the living body by light emitted from the light emitting elements 11, and output the measured light intensity signal as biological information. The light receiving unit 20 may output the measured light intensity signal to the signal processing unit 50 for the purpose of obtaining biological information. Alternatively, the light receiving unit 20 may generate biological information from the measured light intensity signal, and then output the biological information.

The light receiving element 21 preferably includes a photodiode (Photo Detector: PD), and may be a multi-segment PD, a line sensor, an image sensor, or the like, for example, but is not limited to this example.

The light receiving element 21 is also capable of converting the intensity of the light received with the PD into an electrical signal, and output the electrical signal to the signal processing unit described later. The light receiving unit 20 can be a sensor of a charge coupled device (CCD) type, a sensor of a complementary metal oxide semiconductor (CMOS) type, or the like, for example.

The light receiving unit 20 may also include a photodiode (PD), an amplifier circuit, a filter circuit, and an analog-to-digital converter, for example. Further, the light receiving unit 20 may be designed so that the signal processing unit 50 can control the output of detection signals (timings and the like).

In the present technology, one or more light receiving elements 21 such as photodiodes and sensors may be provided in a biological information processing apparatus (a measurement module or the like, for example). Further, in the present technology, one or more light receiving units 20 each including one or more light receiving elements 21 may be provided in a biological information processing apparatus (a measurement module or the like, for example).

The light receiving unit 20 can have one light receiving element that is formed with a light receiving element that receives biologically scattered light with a long coherence length of the light emitting element and has a relatively small light receiving area, and a light receiving element that receives biologically scattered light with a short coherence length and has a relatively large light receiving area. Further, the light receiving unit 20 can have these light receiving elements separately as first and second light receiving elements, respectively.

In a case where light with a long coherence length and light with a short coherence length are to be received by one light receiving element 21, the light receiving unit 20 is preferably designed to adjust light reception by the light receiving element and then control the light reception. With this arrangement, the light receiving element can be used for measuring both an instantaneous value and an interval value, and LDF measurement and PPG measurement can be performed with higher accuracy.

In a case where two light receiving elements 21 are to receive light having a long coherence length and light having a short coherence length, respectively, the light receiving unit 20 is preferably designed so that each light receiving element can measure an interval value and/or an instantaneous value.

Further, the light receiving unit 20 preferably includes at least one light receiving element 21 for measuring both an instantaneous value and an interval value, or at least two light receiving elements that are a first light receiving element 21a for measuring an interval value and a second light receiving element 21b for measuring an instantaneous value.

<1-2(4). Signal Processing Unit 50>

The signal processing unit 50 according to the present technology is designed to be capable of controlling the driving, the irradiation pattern (such as irradiation timing, irradiation time, irradiation interval, and irradiation intensity, for example), and the like of the light emitting unit 10. The signal processing unit 50 may control the driving of the light emitting elements 11 and the like via the light emitting unit 10. The signal processing unit 50 is capable of performing control so that the light emitting elements 11 are driven, with the light emitting time being split.

Further, the signal processing unit 50 is designed to be capable of controlling the driving and the light receiving pattern (such as controlling, light receiving timing, light receiving time, light receiving interval, and light receiving sensitivity of the light receiving element, for example) of the light receiving unit 20. The signal processing unit 50 may control the driving of the light receiving element 21 and the like via the light receiving unit 20. The signal processing unit 50 is capable of performing control so that the light receiving elements 21 are driven, with the light receiving time being split. Further, the signal processing unit 50 may perform control so that the light emitting elements 11 are synchronized with the light receiving element 21.

The signal processing unit 50 may control the light reception adjustment mechanism. The signal processing unit 50 is capable of controlling a light receiving area adjustment mechanism 30. The control to be performed by the light receiving area adjustment mechanism 30 includes: opening/closing control and movement control on the optical filter; control on the number of light receiving PDs and the light receiving intervals of the multi-segment PDs; and control on the received light transmittance (opening/closing control) and the light receiving intervals of a liquid crystal shutter, for example, but are not limited to these examples. Note that the liquid crystal shutter can control light transmittance and function as a shutter (open/close) by modulating the voltage to be applied, and can also be used as a tunable filter.

The signal processing unit 50 can control the first light receiving element 21a that receives biologically scattered light and measures an interval value, and the second light receiving element 21b that receives biologically scattered light and measures an instantaneous value. The signal processing unit 50 can perform these control operations in a case where the first light receiving element 21a measures an instantaneous value or where the second light receiving element 21b measures an interval value. The signal processing unit 50 can control the light emitting elements 11 and the like that emit light to generate the biologically scattered light. The signal processing unit 50 can obtain biological information on the basis of a light intensity signal output from the light receiving element 21, and output the biological information.

In the description below, an example of an embodiment of the present technology will be described, but the present technology is not limited to this example. Further, in the present technology, it is possible to combine the configuration of a device of a first embodiment and the configuration of a device of a second embodiment, as appropriate.

<1-3. Biological Signal Measuring Device 1 According to the First Embodiment>

In the description below, the first embodiment will be described in greater detail with reference to FIGS. 3 to 12, but the present technology is not limited to this embodiment. Explanation of the components that are the same as those explained in <1. Biological Signal Measuring Device According to the Present Technology> described above will not be made below.

The first embodiment the present technology includes: a light emitting unit 10 including at least a first light emitting element 11a and a second light emitting element 11b that irradiate a biological surface; and a light receiving unit 20 that includes at least one light receiving element 21 that receives light scattered in a living body by the light emitted from the light emitting unit. The light receiving unit 20 is designed to output a light intensity signal measured by the light receiving element 21, as biological information.

Further, the light receiving unit 20 in the first embodiment of the present technology preferably includes at least one light receiving element 21 for measuring both an instantaneous value and an interval value. Furthermore, the light receiving unit 20 of the first embodiment preferably includes a light reception adjustment mechanism for the light receiving element 21 to cope with biologically scattered light generated by each light emitted from the light emitting unit 10.

The first light emitting element 11a is preferably designed to emit continuous light between light emissions from the second light emitting element 11b. The second light emitting element 11b is preferably designed to emit pulsed light.

In the first embodiment of the present technology, the light reception adjustment mechanism is used so that one light receiving element (PD) can be used for both LDF measurement and PPG measurement. Thus, influence of noise in signals on LDF and PPG can be reduced. Further, by the present technology, the device can be made smaller in size, and pulse measurement and blood flow measurement can be simultaneously performed in a sophisticated manner. By the present technology, the number of PDs to be driven becomes smaller, and thus, power consumption is lowered. As the PD areas can be made suitable for both LDF and PPG, signals can be acquired with high accuracy. Note that the effects described herein are not necessarily limited thereto, but may also include any of the effects described in the present specification.

<1-3(1). Light Reception Adjustment Mechanism>

In the description below, the light reception adjustment mechanism of the first embodiment of the present technology will be described in detail, but the present technology is not limited to this.

Here, in Patent Document 4, one light receiving element for LDF measurement is also used for PPG measurement, and a PD is shared, as described above. The inventor considered that, in a case where a PD of LDF is used as a PD of PPG as in Patent Document 4, the area of the PD is small, and accordingly, a signal of LDF is not greatly affected by noise when the PD is made to function as a PD of LDF. However, when the PD is made to function as a PD of PPG, a signal of PPG is greatly affected by noise. The inventor also considered that, in a case where a PD of PPG is used as a PD of LDF, on the other hand, the area of the PD is large, and therefore, a signal of PPG is not greatly affected by noise. However, a signal of LDF might be greatly affected by noise. Further, the inventor considered that, in a case where the area of a PD is small, the amount of change in light due to absorption to be measured is smaller, and therefore, the relative influence of noise on a signal of PPG is greater.

As described above, in conventional technologies, in a case where one light receiving element receives biologically scattered light derived from an LDF light source and a PPG light source, the light receiving area and the light receiving distance for obtaining preferred accuracy vary between LDF measurement and PPG measurement, and therefore, a large amount of signal noise is generated in one of them. Therefore, in conventional technologies, in a case where one light receiving element is used as a light receiving element for LDF measurement and a light receiving element for PPG measurement, both pulse measurement and blood flow measurement cannot be performed accurately. That is, in conventional technologies, there is a technical difficulty in integrating light receiving elements into one for LDF and PPG measurement.

In view of the above, the inventor has discovered that the above technical difficulty can be overcome with the use of the light reception adjustment mechanism according to the present technology. Thus, in the first embodiment of the present technology, the light receiving area and/or the light receiving distance (the position or the layout, for example) suitable for both LDF measurement and PPG measurement can be adjusted as appropriate. As a result, both an LDF signal and a PPG signal can be acquired with high accuracy. Further, as a light receiving element is shared, the device that integrates LDF measurement and PPG measurement is made smaller in size. Since a light receiving element is shared, and the number of light receiving elements to be driven is reduced, the device that performs both pulse measurement and blood flow measurement consumes less power.

As described above, by the light reception adjustment mechanism of the present technology, both pulse measurement and blood flow measurement can be performed with high accuracy. With the light reception adjustment mechanism (more preferably, the light receiving area adjustment mechanism) of the present technology, it is possible to perform instantaneous value measurement and interval value measurement with one light receiving element. As the number of light receiving elements can be reduced, the device can be made smaller in size, and its power consumption can also be lowered.

The light receiving area adjustment mechanism 30 provided in the light receiving unit 20 is a means that substantially makes the light receiving area of the light receiving element 21 differ from each of the light emitting elements 11.

The light receiving area adjustment mechanism 30 preferably has a component that reduces the light receiving area for light having a long coherence length and/or a component that increases the light receiving area for light having a short coherence length. Further, the light receiving area adjustment mechanism 30 is preferably adjusted to be a light receiving element that has a relatively smaller light receiving area for light having a long coherence length of a light emitting element than the light receiving area for light having a short coherence length. In the light receiving element, the light receiving area for biologically scattered light of light having a long coherence length is made smaller to increase LDF measurement accuracy. Further, in the light receiving element, the light receiving area for biologically scattered light of light having a short coherence length is made larger to increase PPG measurement accuracy.

The light receiving area adjustment mechanism 30 of the light receiving unit 20 may be an optical filter 31, a multi-segment photodiode 33, a liquid crystal shutter 34, or the like, for example, but is not limited to these examples. More specifically, the light receiving area adjustment mechanism 30 may be an optical filter having a filter portion and an open portion, a multi-segment PD formed by ON/OFF selection, a liquid crystal shutter formed by voltage application, or the like, for example, but is not limited to these examples. It is preferable to use one or more kinds selected from these examples.

A light receiving distance adjustment mechanism of the light receiving unit may be a mechanism for adjusting the position of the light receiving element or adjusting the arrangement between the components, or the like, for example, but is not limited to these examples.

The mechanism for adjusting the position of the light receiving element in the light receiving distance adjustment mechanism is preferably designed to adjust the distance between the light emitting elements 11 and the light receiving element 21 that receives biologically scattered light generated by the light emission. The longer the distance between the biological surface 2 and the light receiving surface of the light receiving element 21, the smaller the influence of signal noise during LDF measurement. Thus, an excellent signal can be obtained. The distance adjustment at this stage may be adjustment of the thickness of the optical filter 31, thickness adjustment by a transparent portion 35, adjustment by a vertical movement mechanism (a rack-and-pinion mechanism or the like, for example), or the like. The transparent portion 35 is not limited to any particular component, but a material having little or no influence on biologically scattered light during LDF measurement and biologically scattered light during PPG measurement is preferable.

A layout adjustment mechanism between the respective components in the light receiving distance adjustment mechanism may be a mechanism or the like for adjusting the layout of the respective light emitting elements 11 and the respective light receiving elements 21, but is not limited to this example. Further, the layout adjustment mechanism between the respective components is preferably designed to adjust the distance between the biological surface 2 and the light receiving surface of the light receiving element 21. Thus, the distances between the respective components can be adjusted as appropriate.

In the description below, an example of the light reception adjustment mechanism of the present technology will be described in detail with reference to FIGS. 3 to 14, but is not limited to this example.

The light reception adjustment mechanism of the present technology may be the light receiving area adjustment mechanism 30 and/or the light receiving distance adjustment mechanism, or the like, for example, but is not limited to this example. Also, these mechanisms may be used independently of each other, of a combination of both mechanisms may be used. As the light receiving area adjustment mechanism is used, a PD area suitable for both LDF measurement and PPG measurement is obtained. Thus, signals in these measurements can be acquired with high accuracy. In the case of the light receiving distance adjustment mechanism that adjusts the distance from a biological surface to the light receiving element, the distance between them is made longer, so that signals in LDF measurement can be acquired with higher accuracy. In the case of the light receiving position adjustment mechanism that adjusts the distance between the light emitting elements and the light receiving element in a plane, the positional relationship between these elements is adjusted, and thus, the depth (the degree of depth) of the blood vessel to be measured in the living body can be adjusted.

<1-3(2). Example 1 of a Biological Signal Measuring Device According to the First Embodiment>

Example 1 of a biological signal measuring device according to the first embodiment of the present technology is now described with reference to FIGS. 3 to 6, but the present technology is not limited to this example. Explanation of the same components as those described above will be skipped as appropriate.

Figure 3:
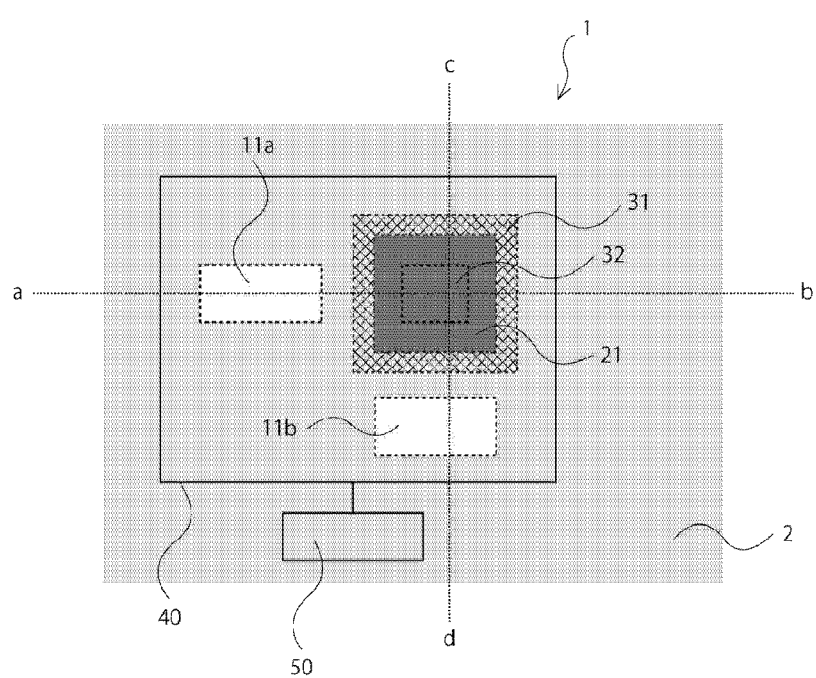
FIG. 3 is a schematic view of an example of a biological signal measuring device according to a first embodiment of the present technology.

FIG. 3 is a schematic view of the biological signal measuring device 1 according to the first embodiment of the present technology.

As shown in FIG. 3, the biological signal measuring device 1 according to the first embodiment includes: a light emitting unit 10 including at least two light emitting elements 11 that cause light to enter the inside of a living body from a biological surface 2; and a light receiving unit 20 including at least one light receiving element 21 that receives light scattered in the living body and outputs a light intensity signal.

The light receiving unit 20 also includes a light reception adjustment mechanism between the biological surface 2 and the light receiving element 21. The light reception adjustment mechanism uses an optical filter 31 that is an example of the light receiving area adjustment mechanism 30. The optical filter 31 has a portion that does not face the light receiving element 21, and this portion is preferably disposed at various distances from the light emitting element having a long coherence length. Further, the structure of the optical filter 31 can adopt various forms including the portion that does not face the light receiving element 21.

The optical filter 31 includes a filter portion and a portion (also referred to as "open portion") 32 (for example, an opening 32 or the like near the center) that opens part of the optical path to the light receiving element instead of covering the entire light receiving element with a filter. The open portion 32 is a portion through which biologically scattered light can pass without passing through the filter portion. In the case of LDF measurement, the filter portion does not allow biologically scattered light of LDF to pass, and the open portion allows biologically scattered light of LDF to pass. In the case of PPG measurement, on the other hand, both the filter portion and the open portion are designed so that biologically scattered light of PPG passes.

The light receiving unit 20 can output a light intensity signal measured by the light receiving element 21, for the purpose of creating biological information. The light receiving unit 20 can also output the light intensity signal measured by the light receiving element 21 as the created biological information. Also, the light receiving unit 20 may perform these operations in cooperation with a signal processing unit 50.

Further, the biological signal measuring device 1 according to the first embodiment may include the signal processing unit 50 that generates biological information on the basis of the light intensity signal output from the light receiving element, and outputs the biological information.

The signal processing unit 50 can control light emission from the light emitting elements and light reception at the light receiving element, by issuing instructions to the light emitting unit 10 and the light receiving unit 20.

The first light emitting element 11a is preferably designed to emit continuous light between light emissions from the second light emitting element 11b. The signal processing unit 50 can perform control so that the first light emitting element 11a emits continuous light between light emissions from the second light emitting element 11b. At this stage, the signal processing unit 50 can perform control so that the biologically scattered light derived from light emission of the first light emitting element is received by the light receiving element 21, and is measured as a light intensity signal for an interval value, and/or perform control so that the biologically scattered light derived from light emission of the second light emitting element is received by the light receiving element 21, and is measured as a light intensity signal for an instantaneous value.

The second light emitting element 11*b* is preferably designed to emit pulsed light. The signal processing unit 50 can perform control so that the second light emitting element 11*b* emits pulsed light, and also control the light receiving element 21 to receive light in response to this.

Also, the biological signal measuring device 1 preferably further includes a housing 40, and the light emitting elements 11, the light receiving element 21, and the optical filter 31 are preferably provided in the housing 40. The light emitting unit 10 and the light receiving unit 20 may be provided in the housing 40, and they may be integrated. With this arrangement, the biological signal measuring device can be easily made smaller in size.

An operation of the first embodiment will be described below as an example with reference to FIGS. 3 to 6, but the present technology is not limited to this example.

As shown in FIG. 3, in the first embodiment, an LD light source (preferably an infrared LD light source) is used as the first light emitting element 11*a*, an LED light source (preferably a visible-light LED) is used as the second light emitting element 11*b*, and further, a combination of portions with transmission characteristics that vary with wavelength can be used as the optical filter 31. With this arrangement, it is possible to provide an optical filter in which the light receiving area of the light receiving element substantially varies for each light emission process. The optical filter 31 preferably prohibits transmission of light of at least one wavelength. The optical filter 31 is preferably designed not to be disposed in the portion that faces the light receiving surface of the light receiving element 21. Further, the open portion 32 through which biologically scattered light passes is preferably provided inside the optical filter.

The material of the optical filter 31 does not allow light having a long coherence length to pass, but preferably allows light having a short coherence length to pass. The specific material of the optical filter is not limited to any particular one, and may be a resin film, glass, or the like. A known material can be selected as appropriate, depending on the target wavelength band. The resin film may be of polycarbonate resin, methacrylic resin, or the like, for example, and the material of the glass may be soda lime glass, quartz glass, or the like, for example, but they are not particularly limited to these examples.

Figure 6:
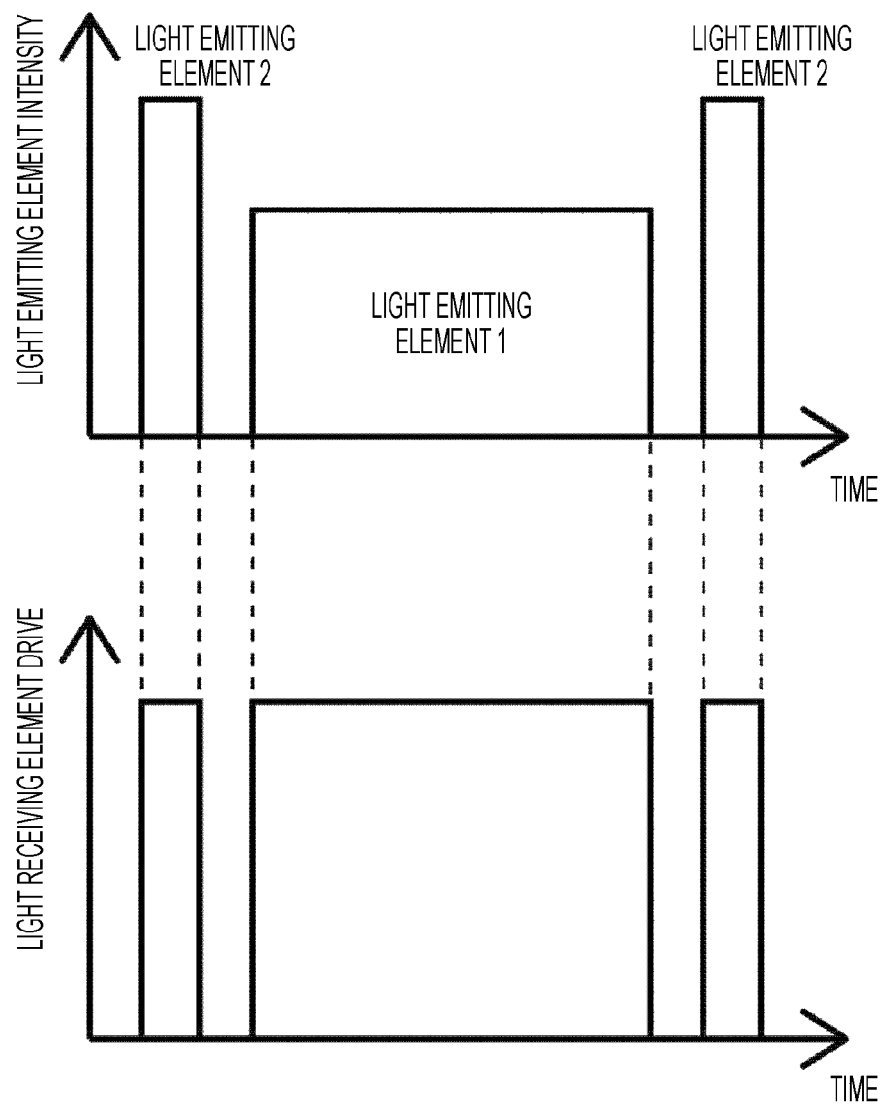
FIG. 6 is a diagram showing an example of split driving when LD light and LED light are emitted and received in the present technology.

As shown in FIG. 6, LD light and LED light are driven in a time-split manner. The split drive can be controlled by the signal processing unit 50. The light receiving element 21 performs sampling and measures an instantaneous value in response to light emission from an LED, and/or continuously measures an interval of light emission in response to light emission from an LD.

Figure 4:
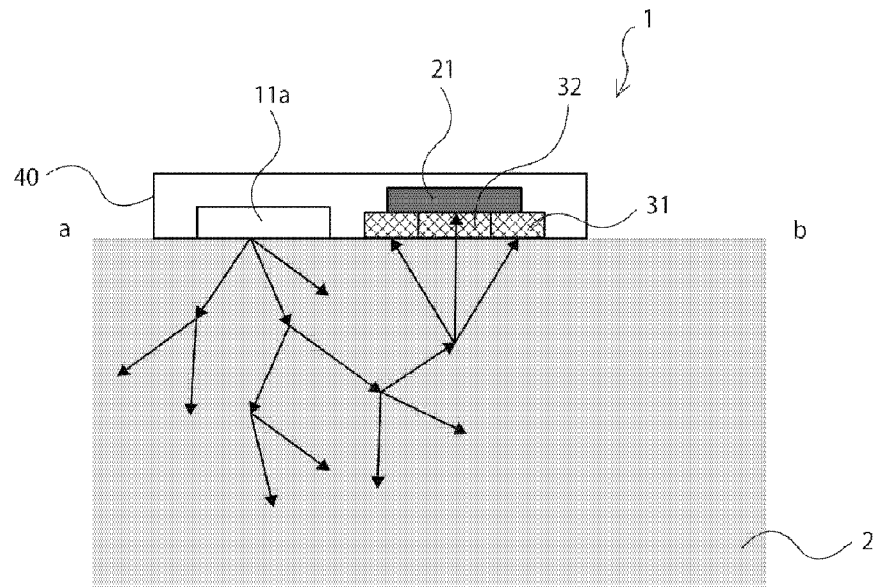
FIG. 4 is an a-b cross-sectional view of the biological signal measuring device according to the first embodiment of the present technology, and is a conceptual diagram of LDF measurement.

Referring now to FIG. 4, a situation in which the light receiving unit 20 of the first embodiment performs LDF measurement is described.

When LDF measurement is performed at the light receiving unit 20, LD-derived biologically scattered light passes through the opening 32 near the center of the optical filter 31, but cannot pass through the optical filter portion other than the opening 32. Therefore, the light receiving element 21 receives the LD-derived biologically scattered light with a small area. At the time of LDF measurement, the biologically scattered light then turns into an excellent signal, as the LDF signal noise becomes smaller with a decrease in the PD light receiving area.

Figure 5:
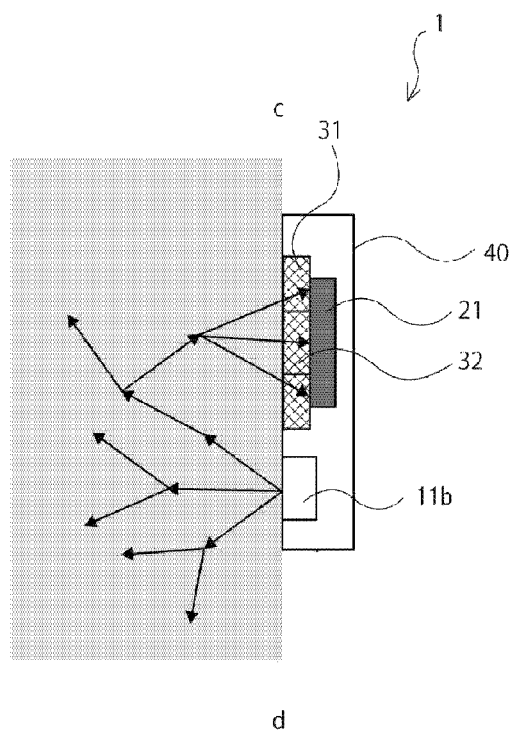
FIG. 5 is a c-d cross-sectional view of the biological signal measuring device according to the first embodiment of the present technology, and is a conceptual diagram of PPG measurement.

Referring now to FIG. 5, a situation in which the light receiving unit 20 of the first embodiment performs PPG measurement is described.

When PPG measurement is performed at the light receiving unit 20, LED-derived biologically scattered light passes through the entire optical filter 31 (specifically, the filter portion and the opening 32). Therefore, the light receiving element 21 receives light with a large light receiving area. At the time of PPG measurement, the biologically scattered light then turns into an excellent signal, because the PPG signal noise becomes smaller with an increase in the PD light receiving area.

As described above, even when a PD is shared between LDF measurement and PPG measurement, the device can be made smaller in size, as the optical filter 31 that is one example of the light reception adjustment mechanism described above is adopted. Furthermore, with this arrangement, pulse and blood flow signals can be measured with higher accuracy.

<1-3(3). Example 2 of a Biological Signal Measuring Device According to the First Embodiment>

Example 2 of a biological signal measuring device according to the first embodiment of the present technology is now described with reference to FIG. 7, but the present technology is not limited to this example. Explanation of the same components as those described above will be skipped as appropriate.

Figure 7:
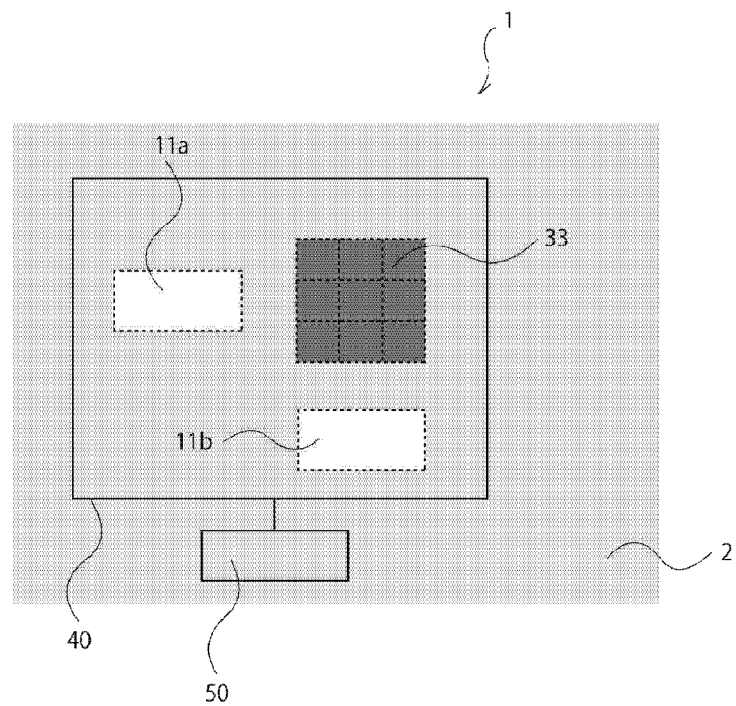
FIG. 7 is a schematic view of an example of a biological signal measuring device according to the first embodiment of the present technology. This is an example case where the biological signal measuring device includes a light reception adjustment mechanism (a multi-segment PD).

As shown in FIG. 7, Example 2 of the biological signal measuring device of the first embodiment is an example case where the light receiving area adjustment mechanism is a mechanism in which a light receiving element is spatially divided, but the present technology is not limited to this example. For example, the light receiving area adjustment mechanism is a multi-segment photodiode 33, a photodiode using a multi-segment liquid crystal shutter, or the like, but the present technology is not limited to this example. In this case, the light emitting elements and the light receiving element are preferably synchronized with one another.

In a case where the multi-segment photodiode 33 is used, the PD of each divided portion preferably adjusts the light receiving area in synchronization with the light emitting elements. In response to light emission from the light emitting element for LDF, the multi-segment PD can be controlled to receive light with a small area. Also, in response to light emission from the light emitting element for PPG, the multi-segment PD can be controlled to receive light with a large area. The control can be performed by the signal processing unit 50 or the like, for example. In the case of a multi-segment PD in which the light receiving unit 20 of the biological signal measuring device is formed with nine segments, for example, the PD of the one segment at the center receives LD-derived biologically scattered light in response to LD light emission, and the PDs of all the nine segments receive LED-derived biologically scattered light in response to LED light emission. Changes in the PD light receiving area may be controlled by the signal processing unit 50. With this arrangement, pulse and blood flow signals can be measured with higher accuracy.

Further, operations of the respective PDs in the multi-segment PD 33 are adjusted, so that the distance relationship between the light emitting elements and the light receiving element can also be adjusted. For example, a PD segment close to the light emitting elements is operated to receive light, so that the measurement depth becomes smaller. A PD segment far from the light emitting elements is operated to receive light, so that the measurement depth becomes greater. With this arrangement, the degree of the measurement depth can be adjusted.

<1-3(4). Example 3 of a Biological Signal Measuring Device According to the First Embodiment>

Example 3 of a biological signal measuring device according to the first embodiment of the present technology is now described with reference to FIG. 8, but the present technology is not limited to this example. Explanation of the same components as those described above will be skipped as appropriate.

Figure 8:
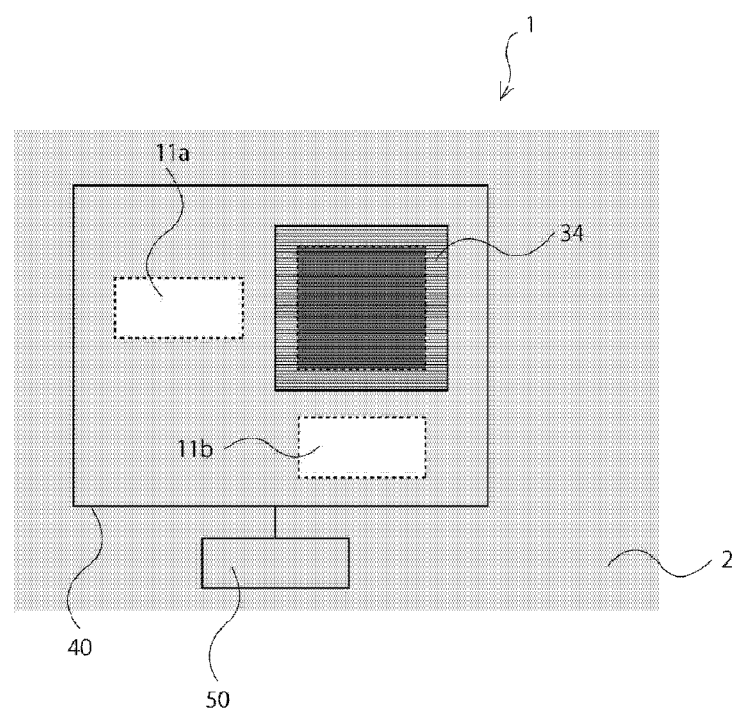
FIG. 8 is a schematic view of an example of a biological signal measuring device according to the first embodiment of the present technology. This is an example case where the biological signal measuring device includes a light reception adjustment mechanism (a liquid crystal shutter).

Example 3 of the biological signal measuring device of the first embodiment is an example case where the light receiving area adjustment mechanism is a mechanism that includes a liquid crystal shutter 34 between the biological surface 2 and the light receiving element 21 as shown in FIG. 8. The liquid crystal shutter 34 can change the light transmission characteristics by changing voltage.

Unlike the optical filter of the present technology, the liquid crystal shutter 34 of the present technology is not provided to face the open portion of the optical filter, but may be provided to face the filter portion of the optical filter. Alternatively, the liquid crystal shutter 34 of the present technology may be a multi-segment liquid crystal shutter like a multi-segment PD.

Application of voltage to the liquid crystal shutter 34 is preferably synchronized with the light emitting elements and the light receiving element, and further adjusts the light receiving area. The light receiving area adjustment mechanism can perform control to receive light with a reduced light receiving area, so that light passes through only a small area of the liquid crystal shutter in response to light emission from the light emitting element for LDF. Also, the light receiving area adjustment mechanism can perform control to receive light with an increased light receiving area, so that light passes through only a large area of the liquid crystal shutter in response to light emission from the light emitting element for PPG. The control can also be performed by the signal processing unit 50 or the like, for example. With this arrangement, pulse and blood flow signals can be measured with higher accuracy.

Further, it is also possible to adjust the distance relationship between the light emitting elements and the light receiving element by adjusting the positions of the light receiving segments in the light receiving area of the light receiving element, using a multi-segment liquid crystal shutter, as described above in the description regarding the multi-segment PD. With this arrangement, the degree of the measurement depth can be adjusted.

<1-3(5). Example 4 of a Biological Signal Measuring Device According to the First Embodiment>

Example 4 of a biological signal measuring device according to the first embodiment of the present technology is now described with reference to FIG. 9, but the present technology is not limited to this example. Explanation of the same components as those described above will be skipped as appropriate.

Figure 9:
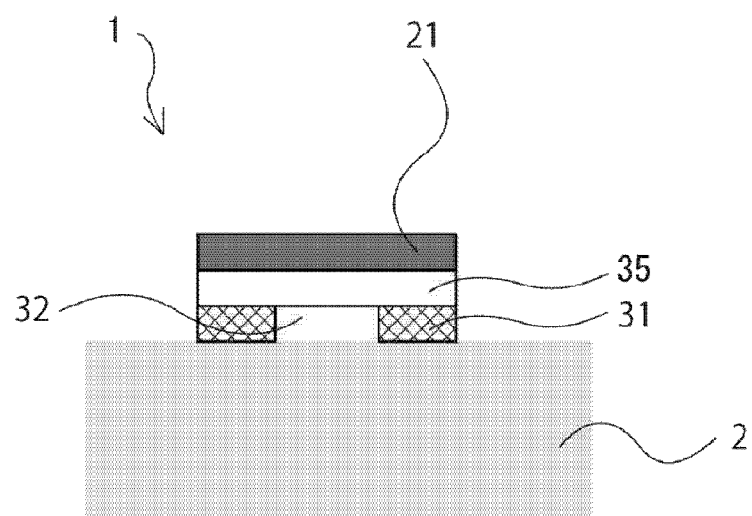
FIG. 9 is a schematic view of an example of a biological signal measuring device according to the first embodiment of the present technology. This is an example case where the biological signal measuring device includes a light reception adjustment mechanism (a transparent portion).

Example 4 of the biological signal measuring device of the first embodiment is an example case where the light receiving distance adjustment mechanism is a mechanism that includes a transparent portion 35 between the biological surface 2 and the light receiving element as shown in FIG. 9. The transparent portion 35 is preferably a member that allows biologically scattered light (more preferably, LDF biologically scattered light) to pass. Further, the transparent portion 35 may have the same open portion as that of the optical filter 31. With this arrangement, pulse and blood flow signals can be measured with higher accuracy, and the device can be made smaller in size.

It is also possible to use the transparent portion 35 and the optical filter 31 in combination. In this case, the transparent portion 35 is preferably disposed at a position facing the light receiving element 21. More preferably, the optical filter 31, the transparent portion 35, and the light receiving element 21 are arranged in this order from the light receiving direction. In this case, it is more preferable to dispose the transparent portion 35 to face the light receiving element 21, and dispose the optical filter 31 on the transparent portion 35.

With this arrangement, pulse and blood flow signals can be measured with higher accuracy, and the device can be made smaller in size.

The material of the transparent portion 35 is not limited to any particular one, and may be a resin film, glass, or the like, for example. A known material can be selected as appropriate, depending on the wavelength band of passing light. The resin film may be of polycarbonate resin, methacrylic resin, or the like, for example, and the material of the glass may be soda lime glass, quartz glass, or the like, for example, but they are not particularly limited to these examples.

The longer the distance between the biological surface 2 and the light receiving surface of the light receiving element 21, the smaller the influence of LDF signal noise. Thus, an excellent signal can be obtained. In FIG. 9, the transparent portion 35 is provided between the light receiving element 21 and the filter opening surface. With this arrangement, LDF measurement and PPG measurement can be performed with higher accuracy.

<1-3(6). Example 5 of a Biological Signal Measuring Device According to the First Embodiment>

Figure 10:
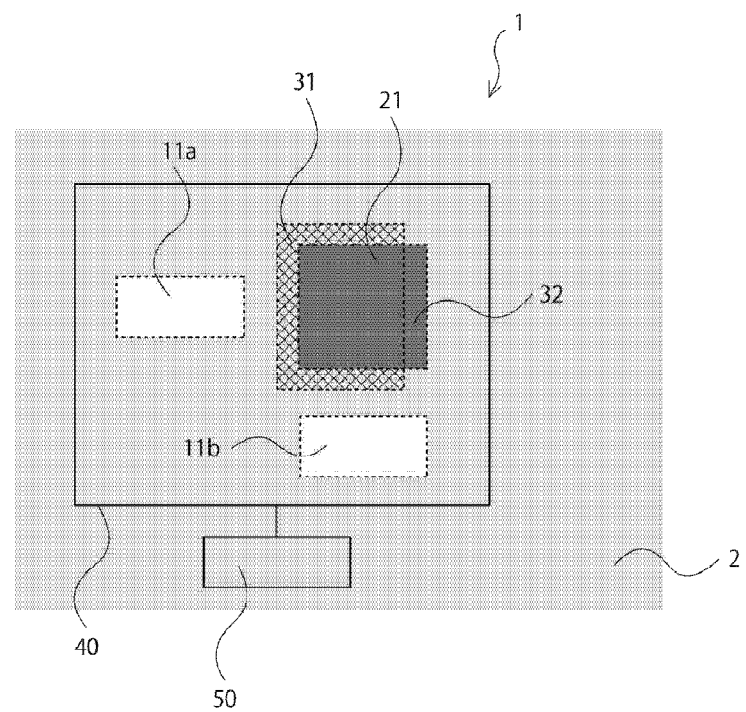
FIG. 10 is a schematic view of an example of a biological signal measuring device according to the first embodiment of the present technology. This is an example case where the biological signal measuring device includes a light reception adjustment mechanism (an optical filter).
Figure 11:
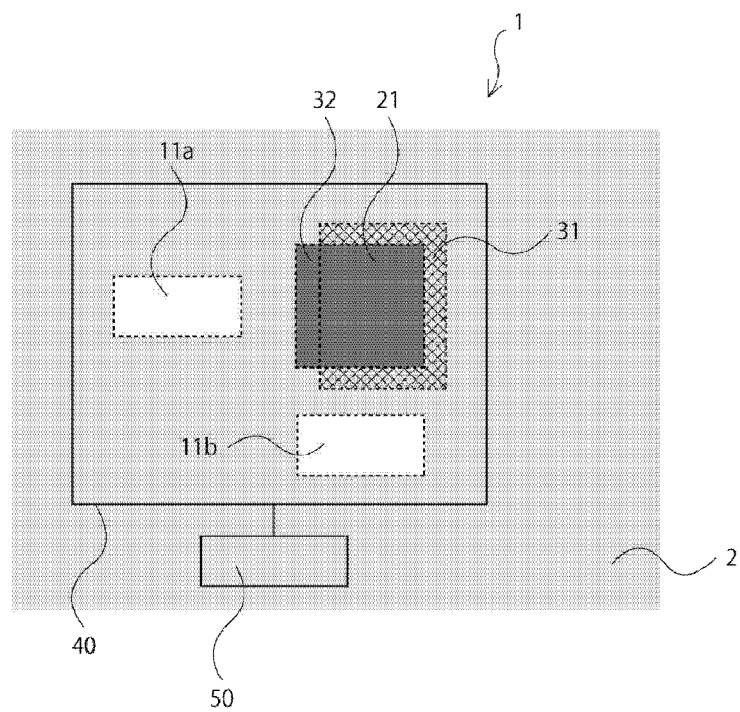
FIG. 11 is a schematic view of an example of a biological signal measuring device according to the first embodiment of the present technology. This is an example case where the biological signal measuring device includes a light reception adjustment mechanism (an optical filter).

Example 5 of a biological signal measuring device according to the first embodiment of the present technology is now described with reference to FIGS. 10 and 11, but the present technology is not limited to this example. Explanation of the same components as those described above will be skipped as appropriate.

Example 5 of the biological signal measuring device of the first embodiment is an example case where the light receiving area adjustment mechanism is a mechanism for adjusting the open portion of the optical filter 31. As a portion (open portion) at which the light receiving surface of the optical filter 31 and the light receiving surface of the light receiving element do not overlap, the open portion 32, which is a portion capable of receiving LDF measurement light, can be provided in the light receiving element 21. The adjustment of the open portion of the optical filter may be performed with a motion mechanism such as a slide mechanism or a rack-and-pinion mechanism, for example, and these can be controlled by the signal processing unit 50 or the like. Alternatively, without the use of any motion mechanism, the open portion of the optical filter may be fixed with an adhesive, a fixing bracket, or the like, after positional relationship of the open portion of the optical filter is adjusted. As it is possible to adjust the light receiving area by adjusting the positional relationship without forming a notch, an opening, or the like in the optical filter 31, the number of steps in the process for manufacturing the optical filter can be reduced, and the light receiving area can be controlled in a simpler manner.

It is possible to adjust the light receiving area to cope with light emission, by adjusting the area of the open portion 32. Accordingly, the light receiving area for LD-derived biologically scattered light can be reduced, and LD-derived biologically scattered light can be received in a preferred manner. Meanwhile, since LED-derived biologically scattered light passes through the optical filter, the light receiving area for LED-derived biologically scattered light can be made larger, and LED-derived biologically scattered light can be received in a preferred manner. With this arrangement, pulse and blood flow signals can be measured with higher accuracy, and the device can be made smaller in size.

Example 5 of the biological signal measuring device of the first embodiment is also an example case where the light receiving position adjustment mechanism is a mechanism for adjusting the position of the open portion of the optical filter 31. As shown in FIGS. 10 and 11, if the distance between the position of the lacking portion 32 in which the optical filter does not exist facing the PD and the light emitting element for LDF varies, blood flow information will also vary. As shown in FIG. 10, the longer the distance between the light emitting element 11 for LDF and the light receiving element 21 (the light receiving portion 32 for LDF), the deeper a blood vessel in the living body can be measured. As shown in FIG. 11, the shorter the distance between the light emitting element 11 for LDF and the light receiving element 21 (the light receiving portion 32 for LDF), the shallower a blood vessels in the living body can be measured. As the position of the optical filter 31 is changed, and the lacking portion (open portion) is adjusted in this manner, the depth (the degree of depth) of the blood vessel to be measured can be changed.

<1-3(7). Example 6 of a Biological Signal Measuring Device According to the First Embodiment>

Example 6 of a biological signal measuring device according to the first embodiment of the present technology is now described with reference to FIG. 12, but the present technology is not limited to this example. Explanation of the same components as those described above will be skipped as appropriate.

Figure 12:
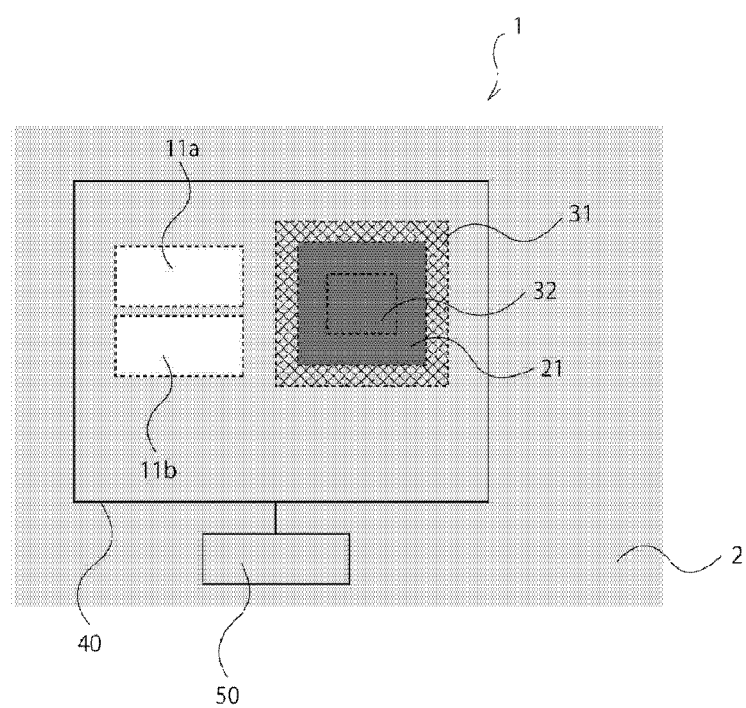
FIG. 12 is a schematic view of an example of a biological signal measuring device according to the first embodiment of the present technology. This is an example case where the positional relationship among the first light emitting element, the second light emitting element, and the light receiving element of the biological signal measuring device is adjusted.

Example 6 of the biological signal measuring device of the first embodiment is an example case where the light receiving distance adjustment mechanism performs adjustment depending on the positional relationship between the light emitting elements 11a and 11b and the light receiving element 21 in a plane as shown in FIG. 12.

The positional relationship between the light emitting elements 11 and the light receiving element 21 may be adjusted with a motion mechanism such as a slide mechanism or a rack-and-pinion mechanism, or may be fixed with an adhesive, a fixing bracket, or the like after adjustment, for example. These operations can be controlled by the signal processing unit 50 or the like. Further, the layout of the light emitting elements 11 and the light receiving element 21 may be adjusted when they are secured to the housing 40.

The longer the distance between the respective light emitting elements 11 for LDF and PPG, and the light receiving element 21, the deeper a blood vessel in the living body can be measured. The shorter the distance between the respective light emitting elements 11 for LDF and PPG, and the light receiving element 21, the shallower a blood vessel in the living body can be measured. As the positions of the light emitting elements and the light receiving element are changed in this manner, the depth (the degree of depth) of the blood vessel to be measured can be changed.

<1-3(8). Examples 7 and 8 of Biological Signal Measuring Devices According to the First Embodiment>

Examples 7 and 8 of biological signal measuring devices according to the first embodiment of the present technology are now described with reference to FIGS. 13 and 14, but the present technology is not limited to these examples. Explanation of the same components as those described above will be skipped as appropriate.

Examples 7 and 8 of the biological signal measuring device each include: a light emitting unit 10 including a first light emitting element 11a and a second light emitting element 11b; and a light receiving unit 20 including an optical filter 31 having a light receiving element 21 and an open portion 32. Further, the light emitting unit 10 and the light receiving unit 20 are preferably housed in a housing 40. Also, a signal processing unit 50 capable of controlling the light emitting unit 10 and the light receiving unit 20 is preferably provided. With this arrangement, pulse and blood flow signals can be measured with higher accuracy, and the device can be made smaller in size.

As shown in FIGS. 3 and 12 and the like, in the light receiving area adjustment mechanism, the optical filter 31 preferably includes a filter portion, and a portion (an opening 32 or the like in the vicinity of the center, for example) that opens part of the light receiving element, instead of covering the light receiving element with a filter.

The open portion is a portion through which biologically scattered light can pass without passing through the filter portion. In the case of LDF measurement, the filter portion does not allow biologically scattered light to pass, and the open portion allows biologically scattered light to pass. In the case of PPG measurement, on the other hand, both the filter portion and the open portion are designed so that biologically scattered light passes. With this arrangement, the accuracy of LDF measurement and PPG measurement can be increased.

The open portion and the shape of the optical filter are not limited to any particular ones, and various forms can be adopted. Further, the open portion may be a space through which light can pass, or may include a material through which coherent light can pass. As for the material, the material of the transparent portion described above is preferable, and examples thereof include plastic resin and glass. However, the material is not limited to any particular one.

Figure 13:
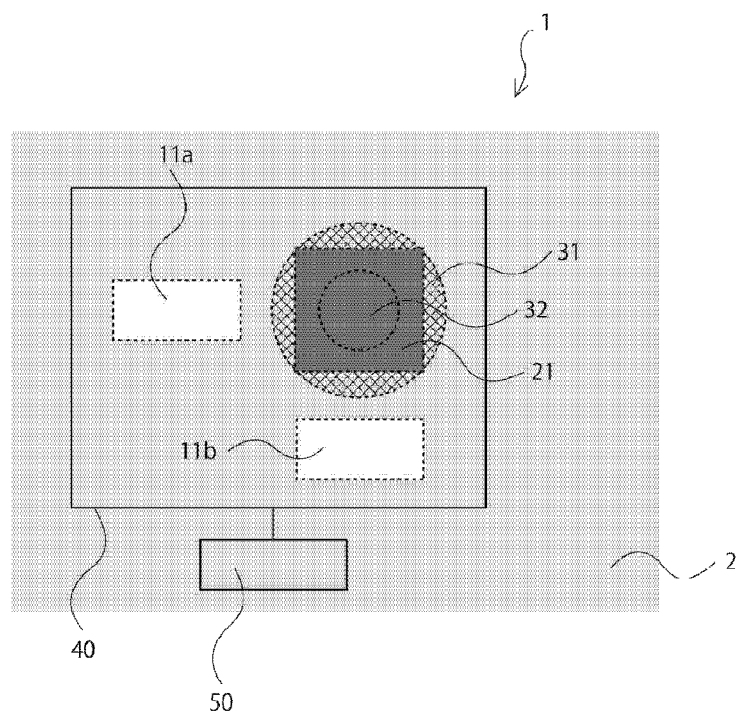
FIG. 13 is a schematic view of an example of a biological signal measuring device according to the first embodiment of the present technology. This is an example case where the biological signal measuring device includes a light receiving area adjustment mechanism (an optical filter).

FIG. 13 shows an example in which the opening (open portion) of the optical filter is circular, but the shape of the opening in the present technology is not limited to any particular one. For example, the shape of the opening may be a polygonal shape (a triangle, a quadrangle, a square, a rectangle, a pentagon, a hexagon, or the like, for example), an elliptical shape, a round shape, a star pattern, or the like.

Figure 14:
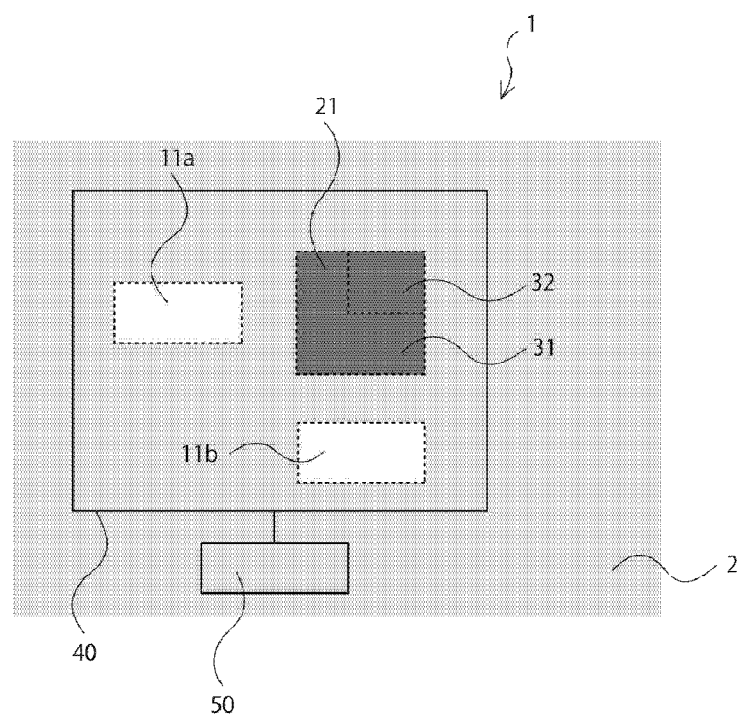
FIG. 14 is a schematic view of an example of a biological signal measuring device according to the first embodiment of the present technology. This is an example case where the biological signal measuring device includes a light receiving area adjustment mechanism (an optical filter).

FIG. 14 shows an example in which the shape of the optical filter has a lacking portion or a cut portion (open portion), but the shape of the filter in the present technology is not limited to any particular one. For example, the shape of the optical filter may be a polygonal shape (a shape having a recessed portion or a protruding portion, a quadrangle, a pentagon, a hexagon, or the like), an elliptical shape, a round shape, a star pattern, or the like.

<1-4. Biological Signal Measuring Device 1 According to the Second Embodiment>

In the description below, the second embodiment will be described in greater detail with reference to FIGS. 15 to 20, but the present technology is not limited to this embodiment. Explanation of the components that are the same as those explained in <1. Biological Signal Measuring Device According to the Present Technology> and the first embodiment described above will not be made below.

The second embodiment the present technology includes: a light emitting unit 10 including at least a first light emitting element 11a and a second light emitting element 11b that irradiate a biological surface; and a light receiving unit 20 that includes at least two light receiving elements 21 that receive light scattered in a living body by the light emitted from the light emitting unit. The light receiving unit 20 is designed to output light intensity signals measured by the light receiving elements 21, as biological information. The layout of the light emitting elements and the light receiving elements is not limited to any particular one.

In the second embodiment of the present technology, a light source can be shared so that a device for LDF measurement and a device for PPG measurement can be integrated into one device. Thus, the resultant device can be made smaller in size. By the present technology, the number of light sources to be driven is reduced, and thus, power consumption is lowered. By the present technology, the intensity of PPG light emission is sufficient, and thus, signals can be acquired with high accuracy. By the present technology, there are two kinds of PPG emission wavelengths, and thus, oxygen saturation and signals for noise removal can be measured. Note that the effects described herein are not necessarily limited thereto, but may also include any of the effects described in the present specification.

The light receiving unit 20 in the second embodiment of the present technology includes at least two light receiving elements: a first light receiving element 21a for interval value measurement and a second light receiving element 21b for instantaneous value measurement. The light receiving unit 20 of the second embodiment has a configuration in which the first light receiving element 21a receives biologically scattered light generated by each light emitted from the light emitting unit 10 and measures an interval value, and the second light receiving element 21b receives the biologically scattered light and measures an instantaneous value.

The first light receiving element 21a for interval value measurement preferably receives biologically scattered light generated by light having a long coherence length of the light emitting element, and/or the second light receiving element 21b for instantaneous value measurement preferably receives biologically scattered light generated by light having a long coherence length of the light emitting element and biologically scattered light generated by light having a short coherence length of the light emitting element. Further, the light receiving area of the first light receiving element 21a is preferably smaller than the light receiving area of the second light receiving element 21b.

The first light emitting element 11a is preferably designed to emit continuous light between light emissions from the second light emitting element 11b. The second light emitting element 11b is preferably designed to emit pulsed light. In this case, the first light receiving element 21a is preferably designed to receive biologically scattered light generated by the continuous light emission from the first light emitting element and measure an interval value, and the second light receiving element 21b is preferably designed to receive biologically scattered light generated by the pulsed light emission from the second light emitting element and part of the biologically scattered light generated by the continuous light emission from the first light emitting element, and measure an instantaneous value.

The first light emitting element 11a is preferably designed to randomly emit continuous light and pulsed light between light emissions from the second light emitting element 11b. The second light emitting element 11b is preferably designed to emit pulsed light. In this case, the first light receiving element 21a is preferably designed to receive biologically scattered light generated by the continuous light emission from the first light emitting element and measure an interval value, and the second light receiving element 21b is preferably designed to receive biologically scattered light generated by the pulsed light emission from the second light emitting element and biologically scattered light generated by the pulsed light emission from the first light emitting element, and measure an instantaneous value.

Further, the distances between the light emitting elements 11 and the light receiving elements 21 that receive the biologically scattered light generated by light emission from the light emitting elements are preferably adjusted. In a case where the adjustment is to be performed in a planar direction, the light receiving distance adjustment mechanism of the first embodiment described above may be adopted, for example. The light receiving distance adjustment is preferably adjustment of the position of the light receiving elements described above, or adjustment of the layout of the respective components, for example. The adjustment of the positions of the light receiving elements by the light receiving distance adjustment mechanism is preferably to adjust the distances between the light emitting elements 11 and the light receiving elements 21 that receive biologically scattered light generated by the light emission. The adjustment of the layout of the respective components by the light receiving distance adjustment is preferably to adjust the layout of the respective light emitting elements 11 and the respective light receiving elements 21.

Further, it is preferable to have a configuration for adjusting the distance between the biological surface 2 and the light receiving surface of each light receiving element 21.

<1-4(1). Example 1 of a Biological Signal Measuring Device According to the Second Embodiment>

Example 1 of the biological device according to the second embodiment of the present technology is now described with reference to FIGS. 15 to 17, but the present technology is not limited to this example. Explanation of the same components as those described above will be skipped as appropriate.

Figure 15:
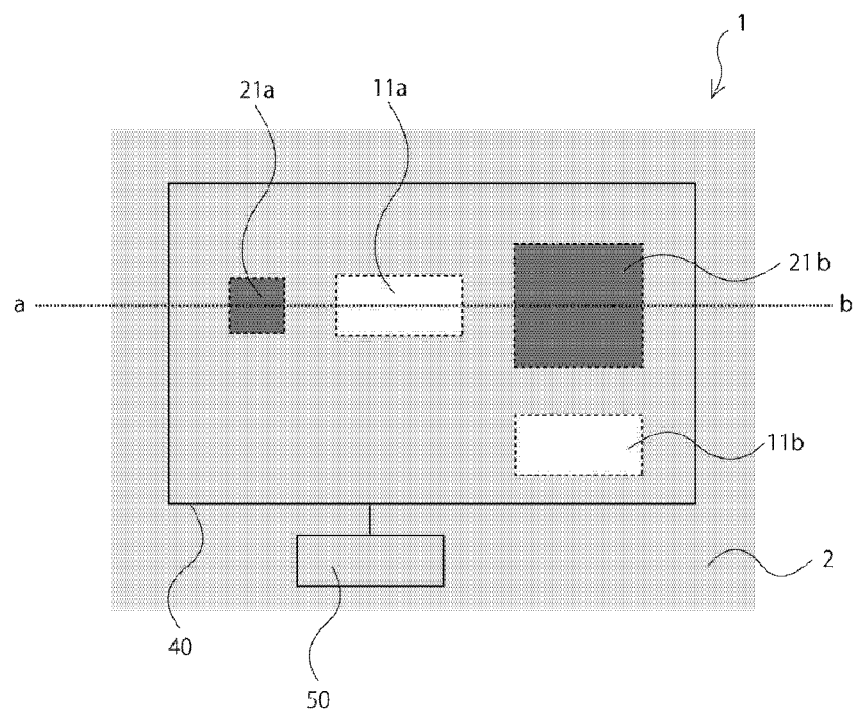
FIG. 15 is a schematic view of an example of a biological signal measuring device according to a second embodiment of the present technology.

FIG. 15 is a schematic view of a biological signal measuring device 1 according to the second embodiment of the present technology.

As shown in FIG. 15, the biological signal measuring device 1 according to the second embodiment includes: a light emitting unit 10 including at least two light emitting elements 11 that cause light to enter the inside of a living body from a biological surface 2; and a light receiving unit 20 including at least two light receiving elements 21 that receive light scattered in the living body and output a light intensity signal. Further, a signal processing unit 50 may be included. The signal processing unit 50 may control operations of the light emitting elements 11 and the light receiving elements 21, and operations of the light emitting unit 10 and the light receiving unit 20. The signal processing unit 50 is designed to be capable of outputting biological information on the basis of light intensity signals output from the light receiving elements.

The light emitting elements are preferably light sources having their wavelength of use in a visible light region, a near-infrared region, or an infrared region. The light receiving elements 21 each preferably include a photodiode (Photo Detector: PD), and may be multi-segment PDs, line sensors, image sensors, or the like, for example, but are not limited to these examples.

Further, the light emitting unit 10 and the light receiving unit 20 are preferably housed in a housing 40.

With this arrangement, pulse and blood flow signals can be measured with higher accuracy, and the device can be made smaller in size.

The light emitting unit 10 includes a first light emitting element 11a and a second light emitting element 11b. The first light emitting element 11a may be a light source that emits light having a long coherence length (so-called coherent light). The second light emitting element 11b may be a light source that emits light having a short coherence length (so-called non-coherent light).

The first light emitting element 11a may be designed to emit continuous light between light emissions from the second light emitting element 11b. The second light emitting element 11b may be designed to emit pulsed light. The first light emitting element 11a may be designed to randomly emit continuous light and pulsed light between light emissions from the second light emitting element 11b.

The light receiving unit 20 includes at least two light receiving elements: a first light receiving element 21a for interval value measurement and a second light receiving element 21b for instantaneous value measurement.

Figure 16:
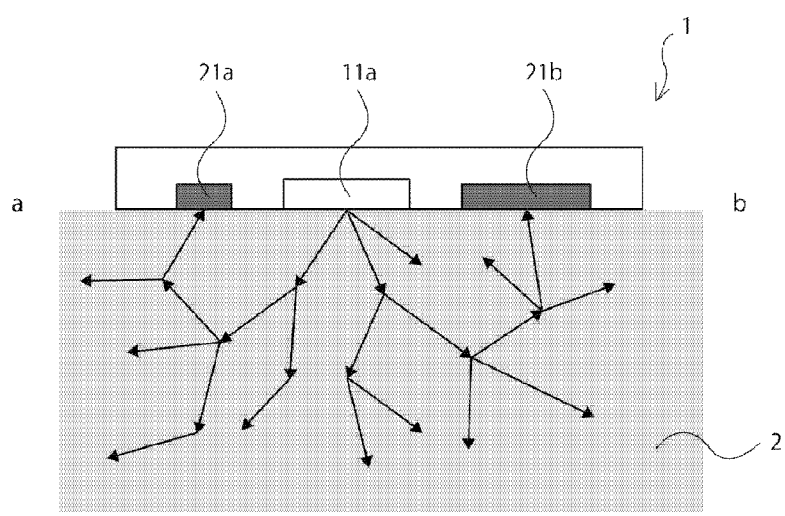
FIG. 16 is an a-b cross-sectional view of the biological signal measuring device according to the second embodiment of the present technology, and is a conceptual diagram of LDF measurement and PPG measurement.
Figure 17:
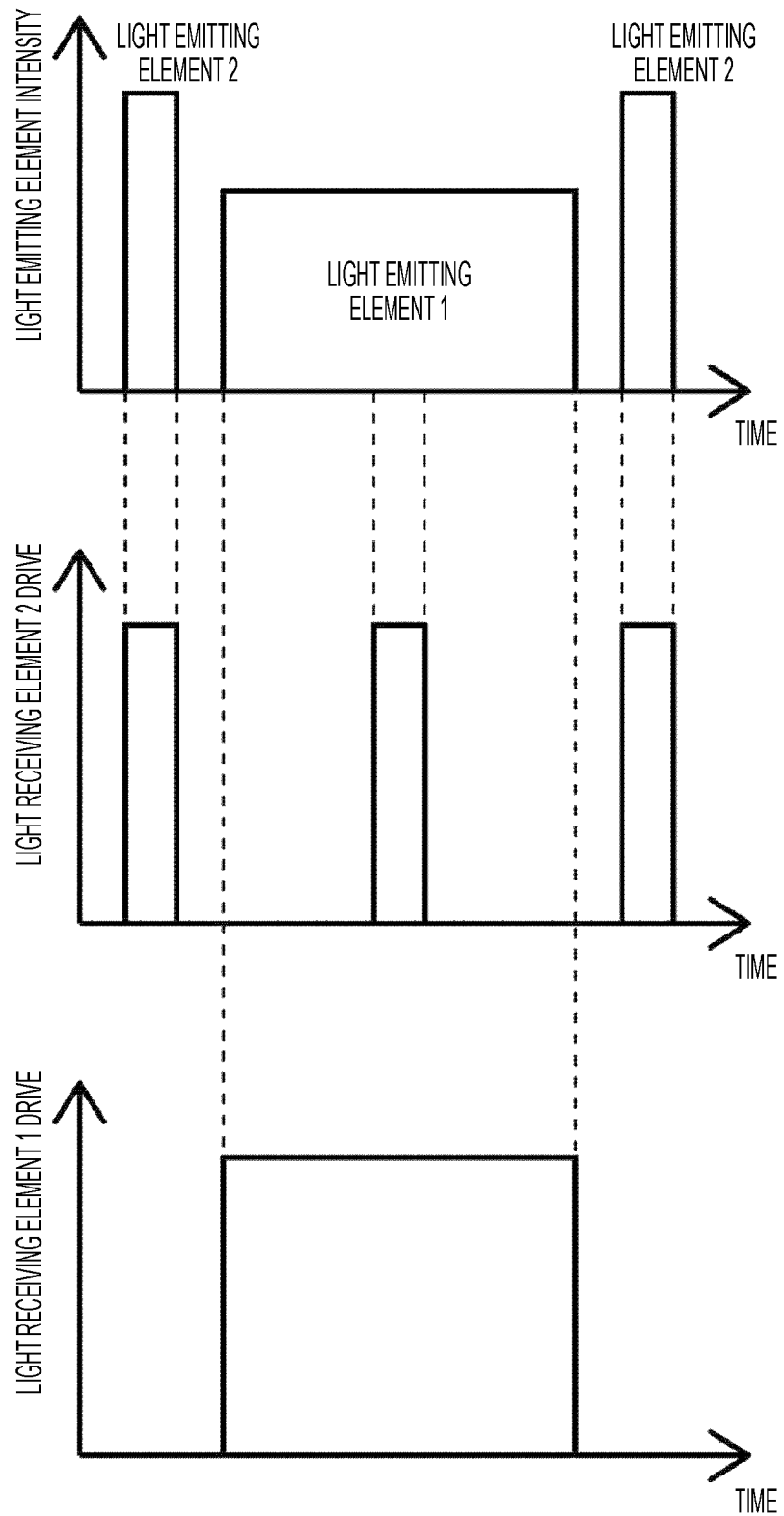
FIG. 17 is a diagram showing an example operation of the biological signal measuring device according to the second embodiment of the present technology.

The light receiving unit 20 preferably has a configuration in which the first light receiving element 21a receives biologically scattered light generated by light emitted from the first light emitting element 11a of the light emitting unit 10, and measures an interval value (the area in drive of light receiving element 1) (see FIGS. 17 and 16). The first light receiving element 21a for interval value measurement is preferably designed to receive biologically scattered light generated by light having a long coherence length of the light emitting element.

The light receiving unit 20 preferably has a configuration in which the second light receiving element 21b receives biologically scattered light generated by light emitted from the second light emitting element 11b of the light emitting unit 10, and measures an instantaneous value (each area in drive of light receiving element 2) (see FIGS. 17 and 16). The second light receiving element 21b for instantaneous value measurement is preferably designed to receive biologically scattered light generated by light having a short coherence length of the light emitting element.

The first light receiving element 21a is preferably designed to receive biologically scattered light generated by continuous light emission from the first light emitting element and measure an interval value, and the second light receiving element 21b is preferably designed to receive biologically scattered light generated by pulsed light emission from the second light emitting element and part of the biologically scattered light generated by the continuous light emission from the first light emitting element, and measure an instantaneous value. Also, the first light receiving element 21a is preferably designed to receive biologically scattered light generated by the continuous light emission from the first light emitting element and measure an interval value, and the second light receiving element 21b is preferably designed to receive biologically scattered light generated by the pulsed light emission from the second light emitting element and biologically scattered light generated by pulsed light emission from the first light emitting element, and measure an instantaneous value.

The light receiving unit 20 can output light intensity signals measured by the light receiving elements 21 as biological information. Also, the light receiving unit 20 may perform these operations in cooperation with a signal processing unit 50.

An operation of Example 1 of the second embodiment will be described below with reference to FIG. 15 and others, but the present technology is not limited to this example.

As shown in FIG. 15, in Example 1 of a biological signal measuring device 1 according to the second embodiment of the present technology, an LD (preferably an infrared LD) is used as the first light emitting element 11a, an LED (preferably a visible-light LED) is used as the second light emitting element 11b, and at least two light emitting elements with different wavelengths are used.

A PD having a smaller light receiving area than that of the second light receiving element 21b is preferably used as the first light receiving element 21a. Further, the light receiving unit 20 including the first light receiving element 21a may include the light reception adjustment mechanism described above.

As shown in FIG. 17, LD light of the first light emitting element 11a and LED light of the second light emitting element 11b are driven in a time-split manner (each area in light emitting element intensity). The second light receiving element 21b performs sampling on light emission from the second light emitting element 11b, and also performs sampling on light emission from the first light emitting element 11a in a similar manner, to measure instantaneous values (each area in drive of light receiving element 2). The first light receiving element 21a measures an intervals at which the first light emitting element 11a emits light with respect to light emission from the first light emitting element 11a (areas of drive of light receiving element 1).

In the case of the second embodiment of the present technology, the second light emitting element 11b as a visible-light LED can emit light that enters a living body with sufficient intensity, and accordingly, measurement can be performed while the influence of PPG signal noise is small. Further, LD light that is emitted from the first light emitting element 11a and is scattered in the living body is received by the PD of the second light receiving element 21b. Accordingly, information with different wavelengths can be acquired in PPG, and signals for noise removal can also be measured from the two different wavelengths. Also, in a case where the two wavelengths of the first light emitting element 11a and the second light emitting element 11b are optimally different, oxygen saturation can be measured with higher accuracy.

As described above, when LDF measurement and PPG measurement are integrated, and a light source is shared, the configuration of Example 1 of the second embodiment is adopted, so that the device can be made smaller in size, and pulse and blood flow signals can be measured with higher accuracy. Further, signals for noise removal can be measured.

Also, two optically different wavelengths are used in PPG, and thus, oxygen saturation can be measured with higher accuracy.

<1-4(2). Example 2 of a Biological Signal Measuring Device According to the Second Embodiment>

An operation of Example 2 of the second embodiment will be described below with reference to FIG. 18 and others, but the present technology is not limited to this example. Explanation of the same components as those described above will be skipped as appropriate. In Example 2 of the second embodiment, the light receiving area adjustment mechanism described above may be used to adjust a relative light receiving area.

Figure 18:
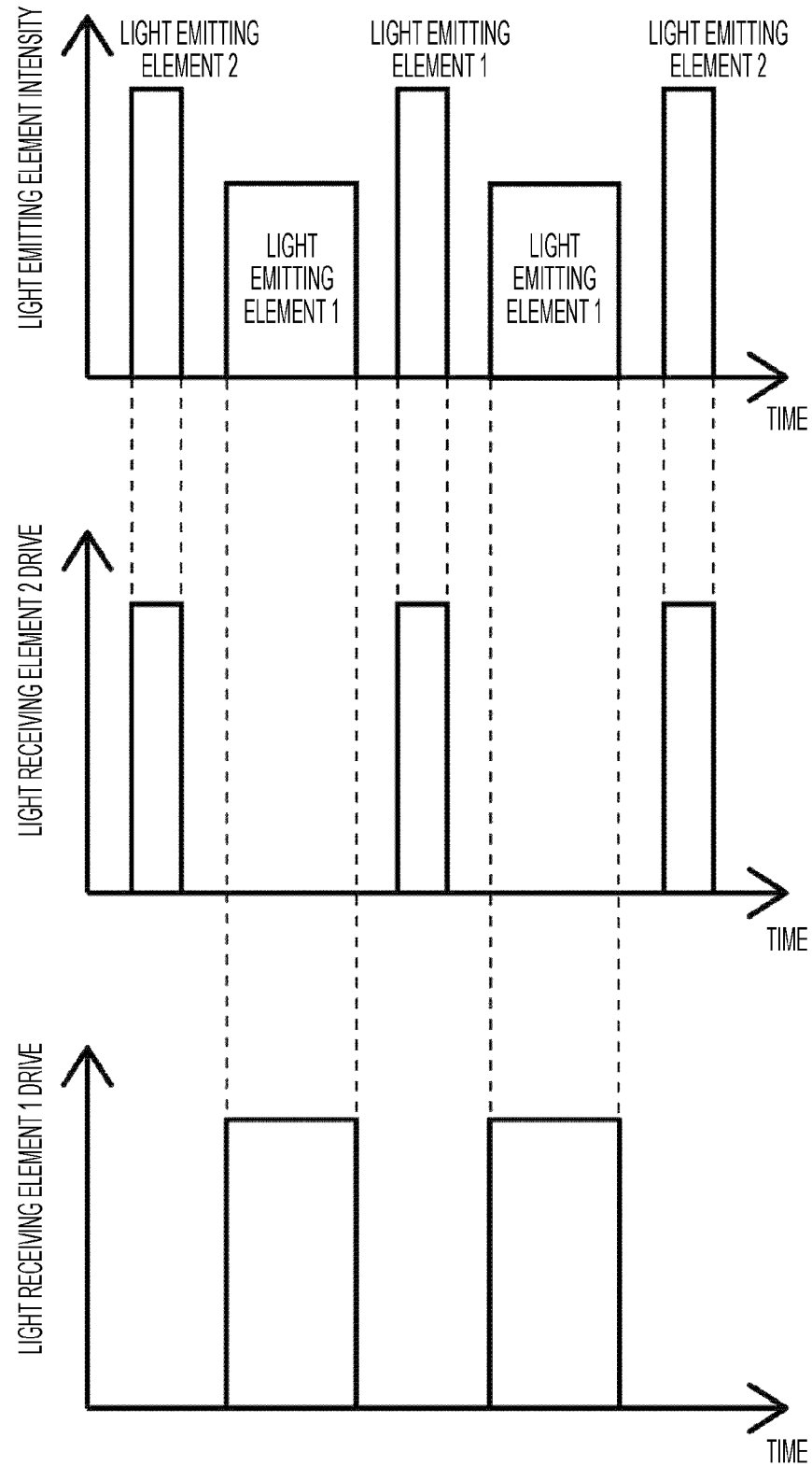
FIG. 18 is a diagram showing an example operation of the biological signal measuring device according to the second embodiment of the present technology.

As shown in FIG. 18, this example is designed so that light having a short coherence length of the second light emitting element 11b is pulsed light, and light having a long coherence length of the first light emitting element 11a has a continuous emission portion and a pulsed emitting portion (each area in light emitting element intensity).

The second light receiving element 21b having the larger light receiving area is designed to perform sampling and measure instantaneous values with respect to pulsed light emission having a short coherence length and pulsed light emission having a long coherence length (each area in drive of light receiving element 2).

The first light receiving element 21a having the smaller light receiving area is designed to measure the light emitting interval with respect to continuous light emission having a long coherence length (each area in drive of light receiving element 1).

Since LD light emission in LDF involves a long light emitting time, it is necessary to lower the light emission intensity to a predetermined value that will not harm the skin and the eyes, from the viewpoint of biosafety. On the other hand, LED light in PPG is instantly emitted as pulsed light, and accordingly, the instantaneous intensity can be made higher than that with LD light. In a case where LD light is used in PPG, part of the LD light is turned into pulsed light, and adjustment is performed so that the LD light has a sufficiently high intensity as a PPG signal. In this case, it is necessary to adjust the intensity to a value that will not cause any problem, from the viewpoint of biosafety.

<1-4(3). Example 3 of a Biological Signal Measuring Device According to the Second Embodiment>

Figure 19:
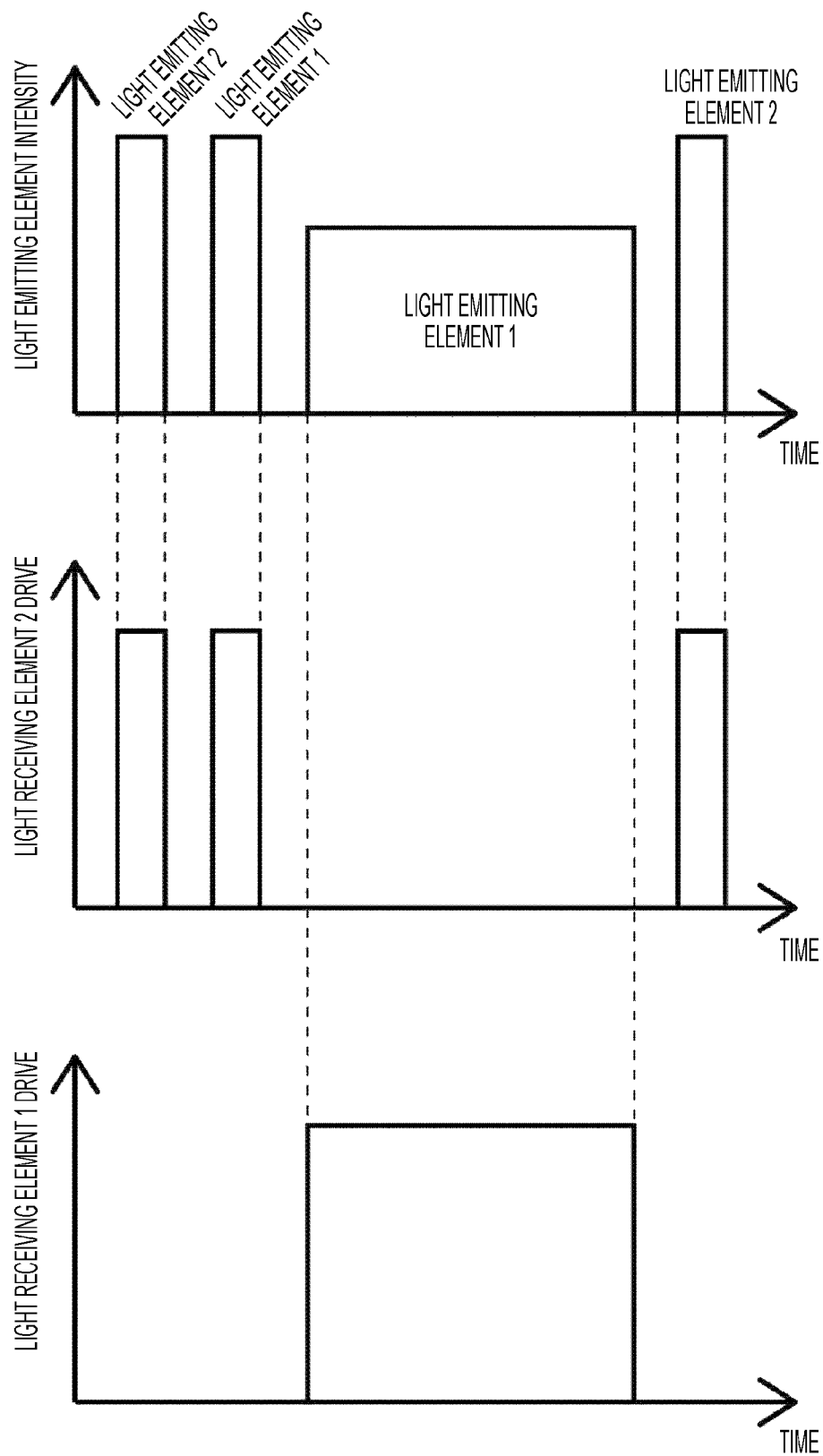
FIG. 19 is a diagram showing an example operation of the biological signal measuring device according to the second embodiment of the present technology.

An operation of Example 3 of the second embodiment will be described below with reference to FIG. 19 and others, but the present technology is not limited to this example. Explanation of the same components as those described above will be skipped as appropriate. In Example 3 of the second embodiment, the light receiving area adjustment mechanism described above may be used to adjust a relative light receiving area.

When light having a short coherence length of the second light emitting element 11b is pulsed light, and light having a long coherence length of the first light emitting element 11a is continuous light or partially pulsed light, the timing of each emission may change in various manners, for example. For example, as shown in FIG. 19, the irradiation intensity of each light emitting element is such that emission can be performed as shown in each area in light emitting element intensity, the second light receiving element 21b can measure an instantaneous value as in each area in drive of light receiving element 2, and the first light receiving element 21a can measure an interval value as in the areas in drive of light receiving element 1.

As described above, the second embodiment of the present technology is not particularly limited to the operations of Examples 1 to 3 described above.

<1-4(4). Example 4 of a Biological Signal Measuring Device According to the Second Embodiment>

Examples 1 and 4 of the second embodiment will be described below with reference to FIGS. 15 and 20 and others, but the present technology is not limited to these examples. Explanation of the same components as those described above will be skipped as appropriate.

Figure 20:
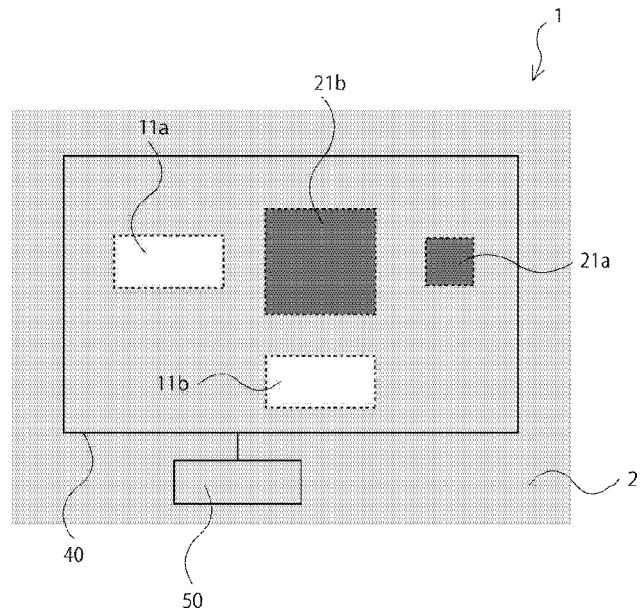
FIG. 20 is a schematic view of an example of a biological signal measuring device according to the second embodiment of the present technology.

As shown in FIGS. 15 and 20, the positional relationship between the first light emitting element 11a that emits LD light and the first light receiving element 21a for LDF can be changed, for example. If the distance between the first light emitting element 11a and the first light receiving element 21a in a planar direction varies, measured blood flow information will vary. In a case where the distance between the light emitting element and the light receiving element is long, at result at a deeper portion in the living body can be measured. On the contrary, in a case where the distance between the light emitting element and the light receiving element is short, a blood vessel at a deeper portion in the living body can be measured. Accordingly, the positional relationship of the light receiving element with respect to the light emitting element is changed, so that the depth (the degree of depth) of the blood vessel to be measured in the living body can be changed. Also, the positional relationship between the second light emitting element 11b that emits LED light and the second light receiving element 21b for PPG is changed, so that the depth (the degree of depth) of the blood vessel to be measured in the living body can be changed.

<2. Biological Information Processing Apparatus>

Figure 21:
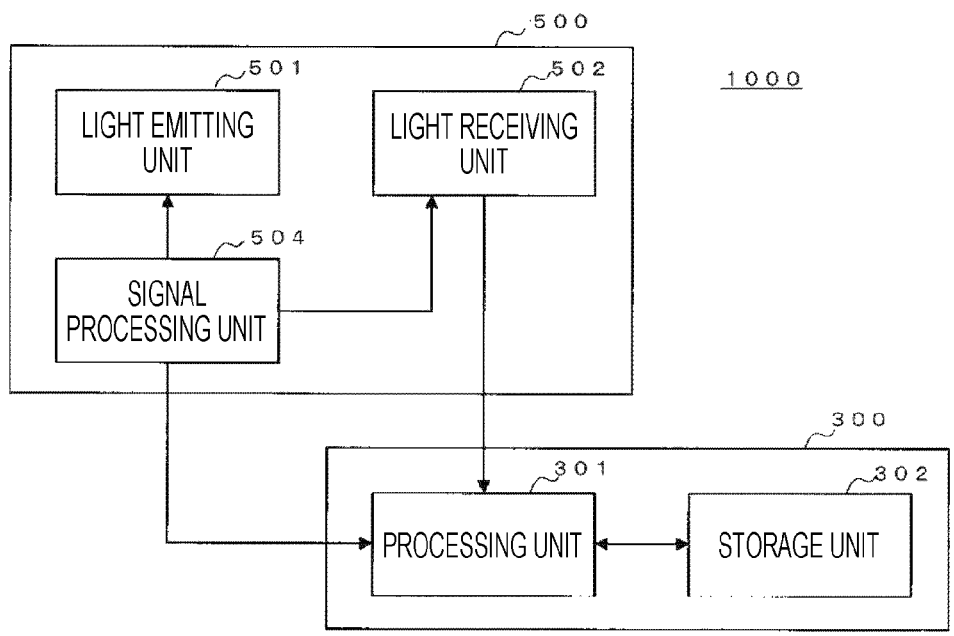
FIG. 21 is a block diagram showing a functional configuration of a biological information processing apparatus 1000 of the present technology.

A biological information processing apparatus 1000 according to the present technology includes a biological signal measuring device 1 of the present technology described above. The biological information processing apparatus 1000 includes: a light emitting unit that includes at least a first light emitting element and a second light emitting element that irradiate a biological surface; and a light receiving unit that includes at least one light receiving element that receives light scattered in a living body by light emitted from the light emitting unit, and outputs biological information that is a light intensity signal measured by the light receiving element (see FIG. 21). Also, the biological information processing apparatus 1000 according to the present technology may be constructed as a system.

The biological signal measuring device 1 of the present technology preferably uses at least two light emitting elements, and is designed to control LDF and/or PPG light reception by adjusting the light receiving area of one light receiving element. Also or alternatively, the biological signal measuring device 1 of the present technology preferably uses at least two light emitting elements, and is designed to control driving related to light emission and light reception so that an interval value and/or an instantaneous value can be measured with the two light receiving elements. Such examples include the biological signal measuring device of the first embodiment and the biological signal measuring device of the second embodiment described above, but the present technology is not limited to these examples.

In an embodiment of the present technology, measurement related to biological information about the subject is performed. More specifically, in an embodiment of the present technology, photoplethysmographic (PPG) measurement and/or laser Doppler blood flowmeter (LDF) measurement is performed, to obtain pulse information and/or blood flow information regarding the pulse and/or the blood flow of the subject. PPG biological information may be pulse information such as pulse rate, pulse wave, and oxygen saturation, oxygen saturation information, and the like, for example. LDF biological information may be blood flow information such as average blood flow velocity, blood flow rate, and velocity distribution of particles in blood vessels, and the like, for example.

In an embodiment of the present technology, to acquire biological information, light is emitted onto the subject's body part (measurement region) such as a hand, an arm, a neck, or a foot, and light scattered in a substance moving in the blood vessels or stationary body tissue of the subject is detected. In this embodiment, the detected light (specifically, a detection signal) is then processed. Thus, PPG measurement biological information and/or LDF measurement biological information can be acquired, and further, pulse information and/or blood flow information and the like can be acquired.

Figure 22:
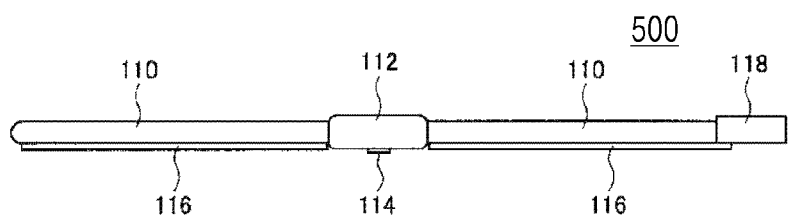
FIG. 22 is a diagram showing an example of an embodiment of a measurement module 500 of the present technology.

The biological information processing apparatus 1000 according to the present technology includes at least a biological signal measuring device 1 of the present technology. Also, in the present technology, a biological information processing system of the present technology that includes at least a biological signal measuring device 1 of the present technology may be constructed, further with the use of various devices, a network, and the like. FIG. 22 shows a measurement module 500 including a biological signal measuring device 1 of the present technology as an example of an embodiment of the biological information processing apparatus 1000 of the present technology. As for the configuration and operation of the biological information processing apparatus 1000, the configurations and operations of Patent Documents 1 to 4 can be referred to, for example, but the present technology is not limited to these examples. The biological information processing apparatus 1000 of the present technology may include an information display device that displays measurement results and the like to a user. The user may be a person who is the measurement target person in PPG measurement and/or LDF measurement, a person who is not the measurement target person and uses the information processing system, or the like.

<Light Emitting Unit 501>

A light emitting unit (also referred to as an irradiation unit) 501 includes at least two light sources (light emitting elements), and emits irradiation light having a predetermined wavelength from the light sources toward the measurement region (a part of the body) of the subject. The light emitting unit 501 is designed to control the driving of each light emission from a first light emitting element and/or a second light emitting element. The wavelength of irradiation light to be emitted from the light emitting unit 501 can be selected as appropriate. A small-sized laser or the like can be used as the light emitting unit 501 to emit light having a long coherence length, and the light emitting unit 501 is capable of emitting a specific wavelength (a wavelength in the neighborhood of 850 nm, for example) from the first light emitting element that is an LD light source, for example. An LED or the like can also be used as the light emitting unit 501 to emit light having a short coherence length, and the light emitting unit 501 is capable of emitting natural light from the second light emitting element that is an LED light source, for example. Further, a signal processing unit (controller) 504, which will be described later, controls the driving and the irradiation pattern (irradiation timing, irradiation time, irradiation intervals, intensity, and the like, for example) of the light emitting unit 501.

<Light Receiving Unit 502>

A light receiving unit (also referred to as a detector) 502 detects light scattered from a measurement region of the subject with a photoreceiver (a PD, for example). The light receiving unit 502 may include the light reception adjustment mechanism (preferably the light receiving area adjustment mechanism) described above.

The light receiving unit 502 includes a photodiode (Photo Detector: PD), for example, converts the intensity of received light into an electrical signal, and outputs the electrical signal to an information processing device 300 described later. Note that the light receiving unit 502 can be a sensor of a charge coupled device (CCD) type, a sensor of a complementary metal oxide semiconductor (CMOS) type, or the like, for example. The light receiving unit 502 may also include a photodiode, an amplifier circuit, a filter circuit, and an analog-to-digital converter, for example. Also, one or a plurality of the photodiodes, the sensors, and the like as described above can be provided in the measurement module 500. The driving and the light receiving conditions (timing and the like, for example) of the light receiving unit 502 are then controlled by the signal processing unit 504 described later.

<Signal Processing Unit 504>

On the basis of a predetermined synchronization signal, the signal processing unit (controller) 504 performs control on all measurement in the measurement module 500, such as control on the irradiation pattern of the light emitting unit 501, and control on the reading (sampling) timing of the light receiving unit 502. For example, the signal processing unit 504 controls the irradiation frequency of the light emitting unit 501 and the sampling frequency of the light receiving unit 502 synchronized with the irradiation frequency, in line with operations of the biological information processing apparatus 1000. The signal processing unit 504 may also include or access a storage unit (not shown), and the storage unit may store various programs, parameters, and the like for controlling the signal processing unit 504 and the like.

Further, the signal processing unit 504 may include a mechanism (a clock mechanism or the like, for example) that obtains other information, to output a detection signal associated with the other information (time or the like, for example) to the information processing device 300. The signal processing unit 504 may be formed with a central processing unit (CPU), a read only memory (ROM), a random access memory (RAM), and the like, for example. Note that some or all of the functions to be executed by the signal processing unit 504 may be executed by the information processing device 300 described later or an accessible information processing device (a server or the like, for example).

<Measurement Module 500>

The measurement module 500 of the present technology includes a power supply for supplying electric power to the light emitting unit 501 and the like. Further, the measurement module 500 may include a communication unit (not shown) that communicates with the information processing device 300 described later and the like, in addition to the light emitting unit 501, the light receiving unit 502, and the signal processing unit 504 described above. The measurement module 500 may also include various sensors (not shown), such as a pressure sensor that detects attachment of the measurement module to a part of the body of the subject, or an acceleration sensor and a gyroscope sensor that detect movement of the body.

The measurement module 500 can also have a form as a wearable device that is worn on the body of the subject at the time of use, for example. For example, the measurement module 500 may be a device that has the shape of a wristwatch, a ring, a wristband, an anklet, a collar, a headset, or the like, and can be attached to a body part of the subject, such as a wrist, an arm, the neck, a leg, or an ear. The measurement module 500 may also be a device that has a pad-like shape like an adhesive bandage, and can be attached to a body part of the subject, such as a hand, an arm, the neck, or a leg. Further, the measurement module 500 may have the shape of an implant to be embedded in a body part of the subject.

Figure 23:
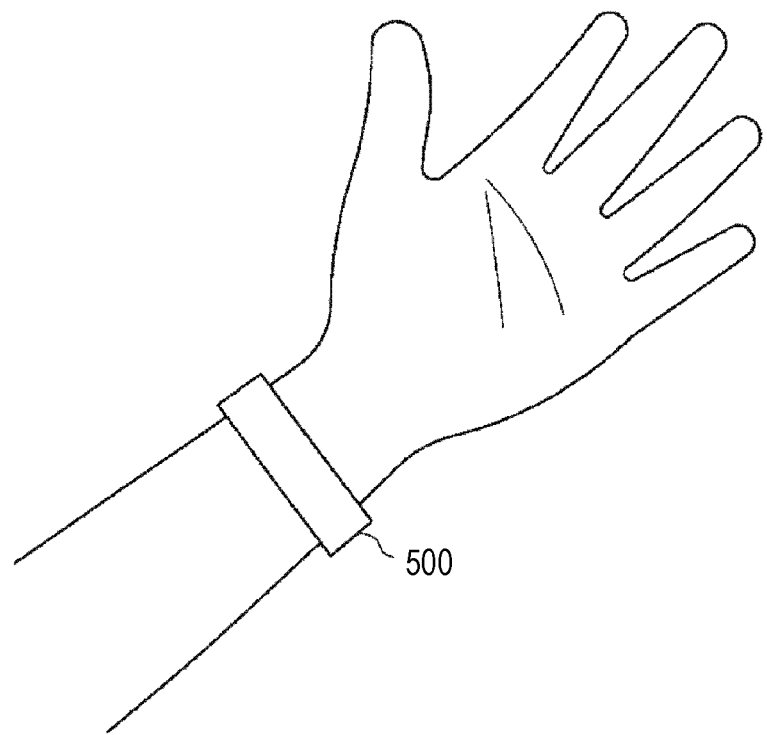
FIG. 23 is a diagram showing an example of an embodiment of a measurement module 500 of the present technology.

In the description below, an example of a specific mode of the measurement module 500 according to the present embodiment is described, with reference to FIGS. 22 and 23. For example, as shown in FIG. 22, the measurement module 500 can have a belt-like shape. As shown in FIG. 22, the measurement module 500 includes a belt-like band portion 110, a control unit 112, and a measurement unit 114. The signal processing unit 504 described above may be provided in the control unit 112. Note that, in a case where the measurement module 500 includes the information processing device 300 described later, each functional unit described later of the information processing device 300 may be provided in the control unit 112. Further, the measurement unit 114 is the portion in which the light emitting unit 501 and light receiving unit 502 described above are provided, and, when the measurement module 500 is attached to a part of the body of the subject, the measurement unit 114 comes into contact with or faces the body.

The band portion 110 is a component for securing the measurement module 500 to a wrist of the subject in a winding manner, for example, and includes a soft material such as silicone gel so as to be turned into a ring-like shape matching the shape of the wrist. As the band portion 110 can be turned into a ring-like shape matching the shape of the wrist, the measurement module 500 can be wound around the wrist of the subject and be secured as shown in FIG. 23. Also, the measurement module 500 is preferably secured onto a measurement region of the subject in which the measurement module 500 does not easily move during measurement of biological information. Therefore, an adhesive layer 116 that can adhere to the skin of the subject may be provided at a portion of the band portion 110 that comes into contact with the skin of the subject. Further, to be able to cope with wrists of various thicknesses, the circumferential length of a ring into which the measurement module 500 is turned is preferably adjusted to any desired length. Therefore, a fixing portion 118 is provided at an end of the band portion 110, and the fixing portion 118 can be fixed at various positions on the band portion 110 when being overlapped with a portion on the band portion 110. In this manner, the measurement module 500 can be attached and secured to a wrist of the subject, coping with the thickness of the wrist.

<Information Processing Device 300>

The information processing device 300 is a device that acquires biological information such as pulse and blood flow information, using detection signals measured by the measurement module 500. The information processing device 300 of the present technology includes at least a processing unit 301 and a storage unit 302. The information processing device 300 may be provided in the measurement module 500, or may be disposed in a component accessible to the measurement module 500.

The processing unit 301 acquires biological information by processing a detection signal obtained by the measurement module 500. The acquired biological information can be output to the storage unit 302, and be also output to other devices.

The storage unit 302 can store the program and various data to be used for processing by the processing unit 301, and further store biological information (PPG measurement biological information, LDF measurement biological information, and the like, for example) acquired by the processing unit 301 and the like. Other than these data and the like, the storage unit 302 may also store parameters, the processing in progress, and the like, as appropriate. The processing unit 301 and the like can freely access the storage unit 302, to write and read data.

Note that the information processing device 300 may include a communication unit (not shown) or the like for communicating with the measurement module and the like. The information processing device 300 may further include an input unit (not shown) or the like that receives an operation from a user who uses the biological information processing apparatus 1000.

Also, the information processing device 300 may be a device integrated with the measurement module 500 described above, or may be a device independent of the measurement module 500. The information processing device 300 may be an information processing device such as a smartphone, a tablet, or a personal computer (PC), for example, or may be an information processing device connected to another device (a medical device or the like, for example). Further, the information processing device 300 may be an information processing device installed at a place far away from the subject, such as a server.

Note that the present technology can also adopt the configurations described below.

[1]

A biological signal measuring device including: a light emitting unit that includes at least a first light emitting element and a second light emitting element that irradiate a biological surface; and a light receiving unit that includes at least one light receiving element that receives light scattered in a living body by light emitted from the light emitting unit, and outputs biological information that is a light intensity signal measured by the light receiving element.

[2]

The biological signal measuring device according to [1], in which the biological signal measuring device performs blood flow measurement and pulse measurement.

[3]

The biological signal measuring device according to [1] or [2], in which the first light emitting element includes at least a light source that emits light having a long coherence length, and the second light emitting element includes at least a light source that emits light having a short coherence length.

[4]

The biological signal measuring device according to any one of [1] to [3], in which the light receiving unit includes at least one light receiving element that measures both an instantaneous value and an interval value, and/or two light receiving elements that measure an instantaneous value and an interval value, respectively.

[5]

The biological signal measuring device according to any one of [1] to [4], in which the light emitting elements are designed to be driven, with a light emitting time being split, and the light receiving element is designed to be driven, with a light receiving time being split.

[6]

The biological signal measuring device according to any one of [1] to [5], in which the light receiving unit includes one light receiving element that measures both an instantaneous value and an interval value, and the light receiving unit includes a light reception adjustment mechanism for the light receiving element to cope with biologically scattered light generated by each light emission from the light emitting unit.

[7]

The biological signal measuring device according to [6], in which the light reception adjustment mechanism of the light receiving unit is designed to reduce a light receiving area of light having a long coherence length.

[8]

The biological signal measuring device according to [6] or [7], in which the light reception adjustment mechanism of the light receiving unit uses at least one of an optical filter, a multi-segment photodiode, or a liquid crystal shutter.

[9]

The biological signal measuring device according to any one of [6] to [8], which is further designed to adjust a distance between the light emitting elements and the light receiving element that receives the biologically scattered light generated by light emission.

[10]

The biological signal measuring device according to any one of [6] to [9], which is further designed to adjust a distance between the biological surface and a light receiving surface of the light receiving element.

[11]

The biological signal measuring device according to any one of [6] to [10], in which the first light emitting element is designed to emit continuous light between light emissions from the second light emitting element.

[12]

The biological signal measuring device according to any one of [6] to [11], in which the second light emitting element is designed to emit pulsed light.

[13]

The biological signal measuring device according to any one of [1] to [12], in which the light receiving unit includes at least two light receiving elements that are a first light receiving element for interval value measurement and a second light receiving element for instantaneous value measurement, and the light receiving unit is designed to receive biologically scattered light generated by each light emission from the light emitting unit with the first light receiving element and measure an interval value, and is designed to receive light with the second light receiving element and measure an instantaneous value.

[14]

The biological signal measuring device according to [13], in which the first light receiving element for interval value measurement is designed to receive biologically scattered light generated by light having a long coherence length of the light emitting elements, the second light receiving element for instantaneous value measurement is designed to receive biologically scattered light generated by light having a long coherence length of the light emitting elements and biologically scattered light generated by light having a short coherence length of the light emitting elements, and a light receiving area of the first light receiving element is smaller than a light receiving area of the second light receiving element.

[15]

The biological signal measuring device according to [13] or [14], in which the first light emitting element is designed to emit continuous light between light emissions from the second light emitting element, the second light emitting element is designed to emit pulsed light, the first light receiving element is designed to receive biologically scattered light generated by the continuous light emission from the first light emitting element, and measure an interval value, and the second light receiving element is designed to receive biologically scattered light generated by the pulsed light emission from the second light emitting element and part of the biologically scattered light generated by the continuous light emission from the first light emitting element, and measure an instantaneous value.

[16]

The biological signal measuring device according to any one of [13] to [15], in which the first light emitting element is designed to randomly emit continuous light and pulsed light between light emissions from the second light emitting element, the second light emitting element is designed to emit pulsed light, the first light receiving element is designed to receive scattered light generated by the continuous light emission from the first light emitting element, and measure an interval value, and the second light receiving element is designed to receive biologically scattered light generated by the pulsed light emission from the second light emitting element and biologically scattered light generated by the pulsed light emission from the first light emitting element, and measure an instantaneous value.

[17]

The biological signal measuring device according to any one of [13] to [16], which is further designed to adjust a distance between the first light emitting element and the light receiving element that receives the biologically scattered light generated by the light emission.

[18]

The biological signal measuring device according to any one of [13] to [16], which is further designed to adjust a distance between the biological surface and a light receiving surface of the light receiving element.

REFERENCE SIGNS LIST

1 Biological signal measuring device
2 Living body (biological surface)
3 Particle that causes light scattering
10 Light emitting unit
11 Light emitting element
11a First light emitting element
11b Second light emitting element
20 Light receiving unit
21 Light receiving element
21a First light receiving element
21b Second light receiving element
30 Light receiving area adjustment mechanism
31 Optical filter
32 Open portion (opening, lacking portion, cut portion)
33 Multi-segment photodiode
34 Liquid crystal shutter
35 Transparent portion
40 Housing
50 Signal processing unit
110 Band portion
112 Control unit
114 Measurement unit
116 Adhesive layer
118 Fixing portion
300 Information processing device
301 Processing unit
302 Storage unit
500 Measurement module
501 Light emitting unit (irradiation unit)
502 Light receiving unit (detector)
504 Signal processing unit (controller)
1000 Biological information processing apparatus (system)

The invention claimed is:

1. A biological signal measuring device, comprising:
a light emitting unit configured to emit light, wherein the light emitting unit includes:
a first light source configured to irradiate a biological surface of a living body in a first time period; and
a second light source configured to irradiate the biological surface in a second time period; and
a light receiving unit that includes:
at least one photoreceiver configured to:
receive scattered light, wherein the light emitted from the light emitting unit is scattered in the living body; and
measure a light intensity signal based on the scattered light, wherein
the light receiving unit is configured to output biological information related to the living body based on the measured light intensity signal; and
a light reception adjustment mechanism that includes a light receiving area adjustment mechanism, wherein the light receiving area adjustment mechanism includes:
a first portion that includes an opening; and
a second portion that includes an optical filter configured to prohibit transmission of light of certain wavelength, wherein the first portion is inside the second portion, wherein
the light receiving area adjustment mechanism is configured to:
allow the scattered light to pass through the opening in the first portion and block the scattered light at the optical filter in the second portion in the first time period; and
allow the scattered light to pass through both the opening in the first portion and the optical filter in the second portion in the second time period.

2. The biological signal measuring device according to claim 1, wherein the biological signal measuring device is configured to perform blood flow measurement and pulse measurement for the living body.

3. The biological signal measuring device according to claim 1, wherein
the first light source is further configured to emit first light having a long coherence length, and
the second light source is further configured to emit second light having a short coherence length.

4. The biological signal measuring device according to claim 1, wherein one of:
the at least one photoreceiver is further configured to measure both an instantaneous value and an interval value, or
the light receiving unit includes two photoreceivers configured to measure the instantaneous value and the interval value, respectively, wherein the two photoreceivers includes the at least one photoreceiver.

5. The biological signal measuring device according to claim 1, further comprising a central processing unit (CPU) configured to:
control the first light source and the second light source to be driven in a time-split manner; and
control the at least one photoreceiver to be driven in the time-split manner.

6. The biological signal measuring device according to claim 1, wherein
the at least one photoreceiver is further configured to measure both an instantaneous value and an interval value.

7. The biological signal measuring device according to claim 1, wherein the light receiving area adjustment mechanism is further configured to reduce a light receiving area of light having a long coherence length.

8. The biological signal measuring device according to claim 1, wherein the light reception adjustment mechanism further includes a liquid crystal shutter.

9. The biological signal measuring device according to claim 1, wherein the light reception adjustment mechanism further includes
a light receiving distance adjustment mechanism configured to adjust a distance between the first light source and the at least one photoreceiver.

10. The biological signal measuring device according to claim 1, wherein the light reception adjustment mechanism is further configured to adjust a distance between the biological surface and a light receiving surface of the at least one photoreceiver.

11. The biological signal measuring device according to claim 1, wherein the first light source is further configured to emit continuous light between light emissions from the second light source.

12. The biological signal measuring device according to claim 1, wherein the second light source is further configured to emit pulsed light.

13. The biological signal measuring device according to claim 1, wherein
the light receiving unit further includes at least two photoreceivers including the at least one photoreceiver,
the at least two photoreceivers include a first photoreceiver for measurement of an interval value and a second photoreceiver for measurement of an instantaneous value,
the first photoreceiver is configured to:
receive first scattered light generated based on light emitted by the first light source scattered in the living body; and
measure the interval value based on the received first scattered light, and
the second photoreceiver is configured to:
receive second scattered light generated based on light emitted by the second light source scattered in the living body; and
measure the instantaneous value based on the received second scattered light.

14. The biological signal measuring device according to claim 13, wherein
the first photoreceiver for the measurement of the interval value is further configured to receive the first scattered light generated based on the light emitted by the first light source having a long coherence length,
the second photoreceiver for the measurement of the instantaneous value is further configured to receive the first scattered light generated based on the light emitted by the first light source having the long coherence length and the second scattered light generated based on the light emitted by the second light source having a short coherence length, and
a light receiving area of the first photoreceiver is smaller than a light receiving area of the second photoreceiver.

15. The biological signal measuring device according to claim 13, wherein
the first light source is further configured to emit continuous light between light emissions from the second light source,
the second light source is further configured to emit pulsed light, the first photoreceiver is further configured to:
   receive the first scattered light generated based on the continuous light emitted from the first light source; and
   measure the interval value based on the received first scattered light, and
the second photoreceiver is further configured to:
   receive the second scattered light generated based on the pulsed light emitted from the second light source and a part of the first scattered light, and
   measure the instantaneous value based on the received second scattered light and the received part of the first scattered light.

16. The biological signal measuring device according to claim 13, wherein
   the first light source is further configured to randomly emit continuous light and first pulsed light between light emissions from the second light source,
   the second light source is further configured to emit second pulsed light,
   the first photoreceiver is further configured to:
      receive the first scattered light generated based on the continuous light emitted from the first light source; and
      measure the interval value based on the received first scattered light, and
   the second photoreceiver is further configured to:
      receive the second scattered light generated based on the second pulsed light emitted from the second light source and the first scattered light; and
      measure the instantaneous value based on the received second scattered light and the received first scattered light.

17. The biological signal measuring device according to claim 13, wherein the light reception adjustment mechanism further includes
   a light receiving distance adjustment mechanism configured to adjust a distance between the first light source and each of the first photoreceiver and the second photoreceiver.

18. The biological signal measuring device according to claim 13, wherein the light reception adjustment mechanism is further
   configured to adjust a distance between the biological surface and a light receiving surface of each of the first photoreceiver and the second photoreceiver.

* * * * *